(12) United States Patent
Kobayashi et al.

US010378029B2

(10) Patent No.: US 10,378,029 B2
(45) Date of Patent: Aug. 13, 2019

(54) METHOD OF PRODUCING CHEMICAL SUBSTANCE

(71) Applicant: Toray Industries, Inc., Tokyo (JP)

(72) Inventors: Koji Kobayashi, Kamakura (JP); Shiomi Watanabe, Kamakura (JP); Kyohei Isobe, Kamakura (JP); Kenji Sawai, Kamakura (JP); Kyungsu Na, Kamakura (JP); Shingo Hiramatsu, Kamakura (JP); Katsushige Yamada, Kamakura (JP)

(73) Assignee: Toray Industries, Inc., Tokyo (JP)

(*) Notice: Subject to any disclaimer, the term of this patent is extended or adjusted under 35 U.S.C. 154(b) by 11 days.

(21) Appl. No.: 14/371,860

(22) PCT Filed: Jan. 11, 2013

(86) PCT No.: PCT/JP2013/050435
§ 371 (c)(1),
(2) Date: Jul. 11, 2014

(87) PCT Pub. No.: WO2013/105651
PCT Pub. Date: Jul. 18, 2013

(65) Prior Publication Data
US 2014/0349354 A1    Nov. 27, 2014

(30) Foreign Application Priority Data

Jan. 13, 2012 (JP) .................................. 2012-005255

(51) Int. Cl.
| | | |
|---|---|---|
| *C12P 7/56* | (2006.01) |
| *C12P 7/08* | (2006.01) |
| *C12P 7/06* | (2006.01) |
| *C12P 7/10* | (2006.01) |
| *C12P 7/18* | (2006.01) |
| *C12P 7/14* | (2006.01) |
| *C12P 7/54* | (2006.01) |
| *C12P 7/60* | (2006.01) |
| *C12P 7/46* | (2006.01) |
| *C12P 13/04* | (2006.01) |
| *C12P 7/40* | (2006.01) |
| *C12P 13/08* | (2006.01) |
| *C12P 7/58* | (2006.01) |

(52) U.S. Cl.
CPC .................. *C12P 7/56* (2013.01); *C12P 7/06* (2013.01); *C12P 7/065* (2013.01); *C12P 7/08* (2013.01); *C12P 7/10* (2013.01); *C12P 7/14* (2013.01); *C12P 7/18* (2013.01); *C12P 7/40* (2013.01); *C12P 7/46* (2013.01); *C12P 7/54* (2013.01); *C12P 7/58* (2013.01); *C12P 7/60* (2013.01); *C12P 13/04* (2013.01); *C12P 13/08* (2013.01); *C12P 2203/00* (2013.01); *Y02E 50/16* (2013.01); *Y02E 50/17* (2013.01)

(58) Field of Classification Search
None
See application file for complete search history.

(56) References Cited

U.S. PATENT DOCUMENTS

2009/0269812 A1* 10/2009 Sawai .................. C12P 13/04
435/88

FOREIGN PATENT DOCUMENTS

| CN | 101255446 | 9/2008 |
|---|---|---|
| EP | 2 330 209 | 6/2011 |
| JP | 11-506934 A | 6/1999 |
| JP | 3041380 B2 | 3/2000 |
| JP | 2001-095597 A | 4/2001 |
| JP | 2003-212888 A | 7/2003 |
| JP | 2005-229821 A | 9/2005 |
| JP | 2006-525029 A | 11/2006 |
| JP | 2009-112289 A | 5/2009 |
| JP | 2010-504756 A | 2/2010 |
| JP | 4770987 B | 9/2011 |
| WO | 2007/097260 A1 | 8/2007 |
| WO | 2010/067785 A1 | 6/2010 |
| WO | 2012/086763 A1 | 6/2012 |

OTHER PUBLICATIONS

Sawai et al., WO/2007/097260, 2007—Translated copy.*
Kurihara et al., JP4770987, 2011—translated copy.*
Thani et al. "Lactic Acid Production by *Lactococcus lactis* in Batch Cultures Using Single and Mixed Sugars" Thai J. Biotechnol. 7, pp. 1-5., 2006.*
Olivier Fond et al., "The acetone butanol fermentation on glucose and xylose. I. Regulation and kinetics in batch cultures," Biotechnology and Bioengineering, vol. 28, Issue 2, Feb. 1986, pp. 160-166 (Abstract).
Karn A. Erlandson et al., "Dissolution of Xylose Metabolism in *Lactococcus lactis*," Applied and Environmental Microbiology, vol. 66, No. 9, Sep. 2000, pp. 3974-3980.
A. Aden et al., "Lignocellulosic Biomass to Ethanol Process Design and Economics Utilizing Co-Current Dilute Acid Prehydrolysis and Enzymatic Hydrolysis for Corn Stover," NREL Technical Report, 2002.
K. Tanaka et al., "Two different pathways for D-xylose metabolism and the effect of xylose concentration on the yield coefficient of L-lactate in mixed-acid fermentation by the lactic acid bacterium *Lactococcus lactis* IO-1," Applied Microbiology and Biotechnology, vol. 60, Issue 1-2, Oct. 2002, pp. 160-167.
Do Yun Kim et al., "Batch and continuous fermentation of succinic acid from wood hydrolysate by *Mannheimia succiniciproducens* MBEL55E," Enzyme and Microbial Technology, vol. 35, Issues 6-7, Dec. 2004, pp. 648-653.

(Continued)

*Primary Examiner* — Thane Underdahl
(74) *Attorney, Agent, or Firm* — DLA Piper LLP (US)

(57) ABSTRACT

A method produces a chemical product by continuous fermentation including filtering a culture liquid of a microorganism(s) through a separation membrane, retaining unfiltered liquid in, or refluxing unfiltered liquid to, the culture liquid, adding a fermentation feedstock to the culture liquid, and recovering a product in the filtrate, wherein the microorganism(s) is/are a microorganism(s) that undergo(es) catabolite repression, and the fermentation feedstock comprises hexose and pentose.

3 Claims, No Drawings

(56) References Cited

OTHER PUBLICATIONS

Supplementary European Search Report dated Jul. 23, 2015 of corresponding European Application No. 13735747.1.
Sawai, H., et al., "A novel membrane-integrated fermentation reactor system: application to pyruvic acid in continuous culture by Torulopsis glabrata," *Bioprocess and Biosystems Engineering*, vol. 34, No. 6, Feb. 12, 2011, 721-725.
Sawai, H., et al., "Membrane-Integrated Fermentation System for Improving the Optical Purity of D-Lactic Acid Produced during Continuous Fermentation," *Bioscience, Biotechnology, and Biochemistry*, vol. 75, No. 12, Dec. 23, 2011, pp. 2326-2332.

\* cited by examiner

METHOD OF PRODUCING CHEMICAL SUBSTANCE

TECHNICAL FIELD

This disclosure relates to a method of producing a chemical product by continuous fermentation using a fermentation feedstock containing hexose and pentose.

BACKGROUND

As the problem of carbon dioxide emission into the atmosphere and energy problems have been actualized, biomass-derived chemical products represented by biodegradable polymer materials such as lactic acid and biofuels such as ethanol have attracted stronger attention as products with sustainability and life cycle assessment (LCA) capability. These biodegradable polymer materials and biofuels are generally produced as fermentation products from microorganisms using as a fermentation feedstock glucose, which is a hexose, purified from edible biomass such as maize. However, use of edible biomass may cause a rise in its price because of competition with food, resulting in an unstable supply of the feedstock. In view of this, attempts are being made to use sugars derived from non-edible biomass such as rice straw as a fermentation feedstock for microorganisms (see WO 2010/067785).

When a sugar derived from non-edible biomass is used as a fermentation feedstock, cellulose, hemicellulose and the like contained in the non-edible biomass are decomposed into sugars by a saccharifying enzyme. In that process, not only hexoses such as glucose, but also pentoses such as xylose are obtained, and as a consequence a mixed sugar of hexose and pentose is used as a fermentation feedstock if a sugar derived from non-edible biomass is used as a fermentation feedstock for a microorganism (see WO '785).

As a fermentation method in which a sugar derived from non-edible biomass, which is a mixed sugar of hexose and pentose, is used as a fermentation feedstock for a microorganism, continuous fermentation may be employed, but the fermentation yield actually achieved by continuous fermentation has not been studied (see WO '785). On the other hand, as known in the art, the culture medium is continuously used for the fermentation in the case of continuous fermentation using a mixed sugar of hexose and pentose as a fermentation feedstock, and therefore the fermentation yield in continuous fermentation is much lower than in batch fermentation since the microorganism continuously undergoes catabolite repression unlike batch fermentation (see Do Yun Kim, Seong Chun Yim, Pyung Cheon Lee, Woo Gi Lee, Sang Yup Lee, Ho Nam Chang, Batch and continuous fermentation of succinic acid from wood hydrolysate by *Mannheimia succiniciproducens* MBEL55E, Enzyme and Microbial Technology, 35, (2004), 648-653). Thus, according to the common technical knowledge, it has been thought that a microorganism that does not undergo catabolite repression has to be used in the fermentation to improve the fermentation efficiency of continuous fermentation using a mixed sugar of hexose and pentose as a fermentation feedstock for a microorganism.

Many microorganisms that undergo catabolite repression are known as microorganisms capable of fermentation production of biodegradable polymer materials and biofuels. On the other hand, it is known that continuous fermentation using a mixed sugar of hexose and pentose as a fermentation feedstock for a microorganism results in a remarkably decreased fermentation yield due to catabolite repression. In view of this, there is a need to improve the fermentation yield in continuous fermentation using a mixed sugar of hexose and pentose as a fermentation feedstock for a microorganism that undergoes catabolite repression.

SUMMARY

We discovered a method of producing a chemical product by continuous fermentation using a mixed sugar of hexose and pentose as a fermentation feedstock for a microorganism, wherein a microorganism that undergoes catabolite repression is subjected to continuous fermentation using a separation membrane.

That is, we provide:

(1) A method of producing a chemical product by continuous fermentation, the method comprising filtering a culture liquid of a microorganism(s) through a separation membrane; retaining unfiltered liquid in, or refluxing unfiltered liquid to, the culture liquid; adding a fermentation feedstock to the culture liquid; and recovering a product in the filtrate, wherein the microorganism(s) is/are a microorganism(s) that undergo(es) catabolite repression, and the fermentation feedstock comprises hexose and pentose.

(2) The method of producing a chemical product according to (1), wherein the concentration of the pentose in the total amount of the filtrate is not more than 5 g/L.

(3) The method of producing a chemical product according to (1) or (2), wherein the weight ratio between the hexose and the pentose contained in the fermentation feedstock is 1:9 to 9:1.

(4) The method of producing a chemical product according to (1) or (2), wherein the fermentation feedstock comprises a biomass-derived sugar liquid.

(5) The method of producing a chemical product according to any one of (1) to (4), wherein the pentose is xylose.

A chemical product can be produced with a high yield in spite of the fact that a mixed sugar of hexose and pentose is used as a fermentation feedstock for a microorganism(s) that undergo(es) catabolite repression.

DETAILED DESCRIPTION

We provide a method of fermentation production of a chemical product by culturing a microorganism(s) using a fermentation feedstock, which method comprises filtering a culture liquid through a separation membrane; retaining unfiltered liquid in, or refluxing unfiltered liquid to, the culture liquid; adding a fermentation feedstock to the culture liquid; and recovering a product in the filtrate, thereby performing continuous fermentation, wherein the microorganism(s) used is/are a microorganism(s) that undergo(es) catabolite repression, and wherein the fermentation feedstock comprises hexose and pentose.

The carbon source in the fermentation feedstock comprises a mixed sugar containing pentose and hexose. Five-carbon sugar, also called pentose, has 5 carbons constituting the sugar. Pentose can be classified into aldopentose, which has an aldehyde group at the 1-position, and ketopentose, which has a ketone group at the 2-position. Examples of aldopentose include xylose, arabinose, ribose and lyxose, and examples of ketopentose include ribulose and xylulose. The pentose may be any pentose as long as it can be metabolized by a microorganism and, in view of the abundance in nature, availability and the like, xylose and arabinose are preferred, and xylose is more preferred.

Six-carbon sugar, also called hexose, has 6 carbons constituting the sugar. Hexose can be classified into aldose, which has an aldehyde group at the 1-position, and ketose, which has a ketone group at the 2-position. Examples of aldose include glucose, mannose, galactose, allose, gulose and talose, and examples of ketose include fructose, psicose and sorbose. The hexose may be any hexose as long as it can be metabolized by a microorganism and, in view of the abundance in nature, availability and the like, glucose, mannose and galactose are preferred, and glucose is more preferred.

The mixed sugar is not limited, and the mixed sugar is preferably a sugar liquid derived from a cellulose-containing biomass known to contain both hexose and pentose. Examples of the cellulose-containing biomass include herbaceous biomasses such as bagasse, switchgrass, corn stover, rice straw and wheat straw; and woody biomasses such as trees and waste building materials. Cellulose-containing biomasses contain cellulose or hemicellulose, which are polysaccharides produced by dehydration condensation of sugars. By hydrolyzing such polysaccharides, sugar liquids which may be used as fermentation feedstocks are produced. The method of preparing the sugar liquid derived from a cellulose-containing biomass may be any method, and examples of disclosed methods of producing such a sugar include a method in which a sugar liquid is produced by acid hydrolysis of a biomass using concentrated sulfuric acid (JP H11-506934 A, JP 2005-229821 A), and a method in which a biomass is subjected to hydrolysis treatment with dilute sulfuric acid and then enzymatically treated with cellulase and/or the like to produce a sugar liquid (A. Aden et al., "Lignocellulosic Biomass to Ethanol Process Design and Economics Utilizing Co-Current Dilute Acid Prehydrolysis and Enzymatic Hydrolysis for Corn Stover" NREL Technical Report (2002)). Further, examples of disclosed methods in which no acids are used include a method in which a biomass is hydrolyzed using subcritical water at about 250 to 500° C. to produce a sugar liquid (JP 2003-212888 A), a method in which a biomass is subjected to subcritical water treatment and then enzymatically treated to produce a sugar liquid (JP 2001-95597 A), and a method in which a biomass is subjected to hydrolysis treatment with pressurized hot water at 240 to 280° C. and then enzymatically treated to produce a sugar liquid (JP 3041380 B). These treatments may be followed by purification of the obtained sugar liquid. An example of the method is disclosed in WO 2010/067785.

The weight ratio between the pentose and the hexose contained in the mixed sugar is not limited, and preferably 1:9 to 9:1 as represented by the ratio of (pentose):(hexose) in terms of the weight ratio between pentose and hexose in the mixed sugar. This is the sugar ratio for cases where the mixed sugar is assumed to be a sugar liquid derived from a cellulose-containing biomass.

The total sugar concentration in the fermentation feedstock is not limited, and preferably as high as possible within the range in which production of the chemical product by the microorganism(s) is not inhibited. More specifically, the concentration of the carbon source in the culture medium is preferably 15 to 500 g/L, more preferably 20 to 300 g/L. When the total concentration is not more than 15 g/L, the effect of improving the yield from pentose may decrease. Further, in cases where the total sugar concentration is low, the production efficiency of the chemical product also decreases.

The hexose concentration in the fermentation feedstock is not limited as long as the total sugar concentration and the ratio between pentose and hexose are within the ranges described above. By use of the method of producing a chemical product, a good yield can be obtained even with a mixed sugar liquid containing hexose at a concentration of not less than 5 g/L.

The fermentation feedstock may preferably be a usual liquid medium containing a carbon source, nitrogen source, inorganic salt, and if necessary, an organic micronutrient(s) such as an amino acid(s) and vitamin(s).

Examples of the nitrogen source include ammonia gas, aqueous ammonia, ammonium salts, urea and nitric acid salts, and other organic nitrogen sources used supplementarily such as oilcakes, soybean-hydrolyzed liquids, casein digests, other amino acids, vitamins, corn steep liquors, yeasts or yeast extracts, meat extracts, peptides such as peptones, and cells of various fermentation microorganisms and hydrolysates thereof. Examples of inorganic salts that may be added as appropriate include phosphoric acid salts, magnesium salts, calcium salts, iron salts and manganese salts.

When the microorganism(s) require(s) a specific nutrient for its/their growth, the nutrient is added as a preparation or as a natural product containing the nutrient. An anti-forming agent is added as required. The culture liquid means a liquid obtained as a result of growth of a microorganism(s) in a fermentation feedstock. The composition of the fermentation feedstock to be added may be changed as appropriate from the composition of the fermentation feedstock used at the beginning of the culture such that the productivity of the chemical product of interest increases.

The porous membrane used as a separation membrane is explained below.

The porous membrane is not limited as long as it has a function to separate a culture liquid obtained by culturing a microorganism(s) in a stirred culture vessel or a stirred bioreactor from the microorganism(s) by filtration. Examples of porous membranes that may be used include porous ceramic membranes, porous glass membranes, porous organic polymer membranes, metal fiber textiles, and non-woven fabrics. Among these, porous organic polymer membranes and ceramic membranes are especially preferred.

The constitution of the porous membrane used as the separation membrane is explained below. The porous membrane has a separation performance and a permeability suitable for the properties and use of the liquid to be processed.

The porous membrane is preferably a porous membrane comprising a porous resin layer in view of the blocking performance, permeability and separation performance, for example, resistance to dirt.

The porous membrane comprising a porous resin layer preferably has the porous resin layer that functions as a separation functional layer on the surface of a porous base material. The porous base material supports the porous resin layer to give strength to the separation membrane.

When the porous membrane has a porous resin layer on the surface of a porous base material, the porous base material may be impregnated with the porous resin layer or may not be impregnated with the porous resin layer, which may be selected depending on the use of the membrane.

The average thickness of the porous base material is preferably 50 μm to 3000 μm.

The porous base material is composed of an organic material and/or inorganic material or the like, and an organic fiber is preferably used. Preferred examples of the porous base material include woven fabrics and non-woven fabrics composed of organic fibers such as cellulose fibers, cellulose triacetate fibers, polyester fibers, polypropylene fibers and polyethylene fibers. More preferably, a non-woven fabric is used since its density can be relatively easily controlled; it can be simply produced; and it is inexpensive.

As the porous resin layer, an organic polymer membrane may be preferably used. Examples of the material of the organic polymer membrane include polyethylene resins, polypropylene resins, polyvinyl chloride resins, polyvinylidene fluoride resins, polysulfone resins, polyethersulfone resins, polyacrylonitrile resins, cellulose resins and cellulose triacetate resins. The organic polymer membrane may be a mixture of resins containing one or more of these resins as the major component. The major component herein means that the component is contained in an amount of not less than 50% by weight, preferably not less than 60% by weight. Preferred examples of the material of the organic polymer membrane include those which can be easily formed by solutions and are excellent in physical durability and chemical resistance such as polyvinyl chloride resins, polyvinylidene fluoride resins, polysulfone resins, polyethersulfone resins and polyacrylonitrile resins. A polyvinylidene fluoride resin or a resin containing it as the major component is most preferably used.

As the polyvinylidene fluoride resin, a homopolymer of vinylidene fluoride is preferably used. Further, as the polyvinylidene fluoride resin, a copolymer with vinyl monomers capable of copolymerizing with vinylidene fluoride is also preferably used. Examples of the vinyl monomers capable of copolymerizing with vinylidene fluoride include tetrafluoroethylene, hexafluoropropylene and ethylene fluoride trichloride.

The porous membrane that may be used as the separation membrane is not limited as long as the microorganism(s) used for fermentation cannot pass through the membrane, and the membrane is preferably selected within the range in which secretions from the microorganism(s) used in the fermentation or particles in the fermentation feedstock do not cause clogging and the filtration performance is stably maintained for a long period. Therefore, the average pore size of the porous separation membrane is preferably not less than 0.01 μm and less than 5 μm. The average pore size is more preferably not less than 0.01 μm and less than 1 μm since, within this range, both a high blocking performance which does not allow leakage of microorganisms and a high permeability can be achieved, and the permeability can be maintained with higher accuracy and reproducibility for a long time.

When the pore size is close to the size of the microorganism(s), the pores may be blocked by the microorganism(s). Therefore, the average pore size of the porous membrane is preferably less than 1 μm. To prevent leakage of the microorganism(s), that is, a decrease in the elimination rate of the microorganism(s), the average pore size of the porous membrane is preferably not too large as compared to the size of the microorganism(s). When a microorganism having a small cell size such as a bacterium is used, the average pore size is preferably not more than 0.4 μm, more preferably less than 0.2 μm.

In some cases, the microorganism(s) may produce substances other than the chemical product of interest, e.g., substances that are likely to aggregate such as proteins and polysaccharides. Further, in some cases, death of a part of the microorganism(s) in the fermentation culture liquid may produce cell debris. The average pore size is still more preferably not more than 0.1 μm to prevent clogging of the porous membrane due to these substances.

When the average pore size is too small, the permeability of the porous membrane decreases, and thus an efficient operation cannot be carried out even with a clean membrane. Therefore, the average pore size of the porous membrane is preferably not less than 0.01 μm, more preferably not less than 0.02 μm, still more preferably not less than 0.04 μm.

The average pore size can be determined by measuring the diameters of all pores which can be observed within an area of 9.2 μm×10.4 μm under a scanning electron microscope at a magnification of 10,000×, and then averaging the measured values. Alternatively, the average pore size can be determined by taking a picture of the membrane surface under a scanning electron microscope at a magnification of 10,000×, and randomly selecting not less than 10 pores, preferably not less than 20 pores, followed by measuring the diameters of these pores and calculating the number average. When a pore is not circular, its size can be determined by a method in which a circle whose area is equal to the area of the pore (equivalent circle) is determined using an image processing device or the like and then the diameter of the equivalent circle is regarded as the diameter of the pore.

The standard deviation σ of the average pore size of the porous membrane is preferably not more than 0.1 μm. The standard deviation σ of the average pore size is preferably as small as possible. The standard deviation σ of the average pore size is calculated according to Equation 1 below, wherein N represents the number of pores observable within the above-mentioned area of 9.2 μm×10.4 μm, $X_k$ represents the respective measured diameters, and X(ave) represents the average of the pore diameter.

$$\sigma = \sqrt{\frac{\sum_{k=1}^{N}(X_k - X(\text{ave}))^2}{N}} \quad (1)$$

In the porous membrane, permeability to the fermentation culture liquid is one of the important performances. As an index of permeability, the pure water permeability coefficient of the porous membrane before use can be employed. The pure water permeability coefficient of the porous membrane is preferably not less than $5.6 \times 10^{-10}$ m³/m²/s/pa when calculated by measuring the amount of permeation of water with a head height of 1 m using purified water at a temperature of 25° C. prepared with a reverse osmosis membrane. When the pure water permeability coefficient is from $5.6 \times 10^{-10}$ m³/m²/s/pa to $6 \times 10^{-7}$ m³/m²/s/pa, an amount of permeation which is practically sufficient can be obtained.

The surface roughness is the average of the height in the direction vertical to the surface. The membrane surface roughness is a factor that influences how easily a microorganism attached to the surface of a separation membrane is detached by the effect of washing the membrane surface with flowing liquid generated by stirring or a circulating pump. The surface roughness of the porous membrane is not limited as long as it is within the range in which the microorganism(s) and other solids attached to the membrane can be detached. The surface roughness is preferably not more than 0.1 μm. In cases where the surface roughness is not more than 0.1 μm, the microorganism(s) and other solids attached to the membrane can be easily detached.

We found that an operation that does not require excessive power to wash the membrane surface can be carried out more easily by using, more preferably, a porous membrane having a membrane surface roughness of not more than 0.1 μm, an average pore size of not less than 0.01 μm and less than 1 µm, and a pure water permeability coefficient of not less than $2 \times 10^{-9}$ m$^3$/m$^2$/s/pa. When the surface roughness of the porous membrane is not more than 0.1 µm, the shear force generated on the membrane surface during filtration of the microorganism(s) can be reduced. Hence, destruction of the microorganism(s) and clogging of the porous membrane can be suppressed. Thus, long-time stable filtration can be more easily carried out. Further, when the surface roughness of the porous membrane is not more than 0.1 µm, continuous fermentation can be carried out with a smaller transmembrane pressure difference. Therefore, even when clogging of the porous membrane has occurred, a better washing recovery performance can be obtained as compared to cases where the operation was carried out with a larger transmembrane pressure difference. The surface roughness of the porous membrane is preferably as small as possible since suppression of clogging of the porous membrane allows stable continuous fermentation.

The membrane surface roughness of the porous membrane herein is measured using the following atomic force microscope (AFM) under the following conditions:

Device
  Atomic force microscope ("Nanoscope IIIa," manufactured by Digital Instruments, Inc.) Conditions
  Probe:
    SiN cantilever (manufactured by Digital Instruments, Inc.)
  Scanning mode:
    Contact mode (measurement in air)
    Underwater tapping mode (underwater measurement)
  Scanning area:
    10 µm×25 µm (measurement in air)
    5 µm×10 µm (underwater measurement)
  Scanning resolution:
    512×512

Sample Preparation

When the measurement was carried out, the membrane sample was soaked in ethanol at room temperature for 15 minutes and then soaked in RO water for 24 hours to wash it, followed by drying in the air. The RO water means water prepared by filtration through a reverse osmosis membrane (RO membrane), which is a type of filtration membrane, to remove impurities such as ions and salts. The pore size of the RO membrane is not more than about 2 nm.

The membrane surface roughness $d_{rough}$ is calculated according to Equation 2 below based on the height of each point in the direction of the Z-axis, as determined using the atomic force microscope (AFM).

$$d_{rough} = \sum_{n=1}^{N} \frac{|Z_n - \overline{Z}|}{N} \qquad (2)$$

$d_{rough}$: Average surface roughness (µm)

$Z_n$: Height in the direction of the Z-axis (µm)

$\overline{Z}$: Average height in the scanned area (µm)

The shape of the porous membrane is preferably a flat membrane. When the shape of the porous membrane is a flat membrane, its average thickness is selected depending on its use. The average thickness in the cases where the shape of the porous membrane is a flat membrane is preferably 20 µm to 5000 µm, more preferably 50 µm to 2000 µm. Further, the shape of the porous membrane is preferably a hollow fiber membrane. When the porous membrane is a hollow fiber membrane, the inner diameter of the hollow fiber is preferably 200 µm to 5000 µm, and the membrane thickness is preferably 20 µm to 2000 µm. A fabric or knit produced by forming organic fibers or inorganic fibers into a cylindrical shape may be contained in the hollow fiber.

The porous membrane described above can be produced by, for example, the production method described in WO 2007/097260.

Preferably, the separation membrane may be a membrane containing at least a ceramic. The ceramic means a substance that contains a metal oxide and was baked by heat treatment at high temperature. Examples of the metal oxide include alumina, magnesia, titania and zirconia. The separation membrane may be formed by only a metal oxide(s), or may contain silica and/or silicon carbide, and/or mullite and/or cordierite, which are compounds of silica and a metal oxide(s).

Components forming the separation membrane other than the ceramic are not limited as long as the components can form a porous body as a separation membrane.

Even when the separation membrane contains a ceramic, the shape of the separation membrane is not limited, and may be any of a monolith membrane, flat membrane, tubular membrane and the like. In view of the efficiency of packing into a container, the separation membrane preferably has a columnar shape in which a penetrating hole(s) is/are formed in the longitudinal direction. In view of increasing the packing efficiency, the separation membrane is preferably a monolith membrane.

The reason why the separation membrane preferably has a penetrating hole(s) in the longitudinal direction is as follows. When a separation membrane having a columnar structure is placed in a modular container to use it as a separation membrane module, modularization of the separation membrane is possible by selecting a preferred mode from the external-pressure type and the internal-pressure type, and filtration can be carried out with the module. The side in which the separation membrane contacts with the fermentation culture liquid is hereinafter referred to as the primary side, and the side in which a filtrate containing a chemical product is obtained by filtration is hereinafter referred to as the secondary side.

When an inner-pressure type module is used, the channel in the primary side is narrow. Therefore, the output of the circulating pump during cross-flow filtration can be saved. Further, the action to discharge the suspended matter accumulated on the surface of the separation membrane is strong and, therefore, the surface of the separation membrane is likely to be kept clean, which is preferred. However, to obtain this effect, the inner-pressure type separation membrane needs to have an inlet and an outlet for the fermentation culture liquid. The inlet and the outlet are preferably in a state where they are arranged on a straight line to form a penetrating hole since the flow resistance is small in such a case. Further, when the separation membrane has a columnar shape and the penetrating hole(s) open(s) in the longitudinal direction, the container containing the separation membrane can be made thin. A thin separation membrane module is preferred in view of production and handling.

The porosity of the separation membrane is not limited, but when the porosity is too low, the filtration efficiency is low; and when the porosity is too high, the strength is low. The porosity is preferably 20% to 60% to achieve both high filtration efficiency and high strength of the separation membrane, as well as resistance to repeated steam sterilization.

The porosity is determined according to the following equation:

Porosity [%]=100×(wet membrane weight [g]−dry membrane weight [g])/specific gravity of water [g/cm³]/(membrane volume [cm³]).

The average pore size of the separation membrane is preferably 0.01 μm to 1 μm, and a membrane having an average pore size within this range is less likely to be clogged and has excellent filtration efficiency. Further, with an average pore size of 0.02 μm to 0.2 μm, substances that easily cause clogging of a separation membrane such as by-products of fermentation by the microorganism or cultured cells, including proteins and polysaccharides, and cell debris produced by death of the microorganism/cultured cells in the culture liquid, become less likely to cause clogging, which is especially preferred.

In a separation membrane having a penetrating hole(s) and a columnar structure, the outer surface is in the secondary side. Therefore, it is preferred that a modular container be provided to collect the filtrate and that the separation membrane be packed into the container to form a module to be used. One or more separation membranes are packed into one module.

The modular container is preferably composed of a material resistant to repeated steam sterilization. Examples of the material resistant to steam sterilization include stainless steels, and ceramics having low average porosities.

Such a ceramic membrane module can be produced by, for example, the production method described in WO 2012/086763, or a commercially available module may be used. Specific examples of the commercially available module include MEMBRALOX Microfiltration Membrane (Pall Corporation) and a ceramic membrane filter Cefilt MF Membrane (NGK Insulators, Ltd.).

Next, the continuous fermentation is explained below.

In the method of producing a chemical product, the transmembrane pressure difference during filtration is not limited as long as the fermentation culture liquid can be filtered. However, when filtration treatment is carried out for filtration of a culture liquid through an organic polymer membrane with a transmembrane pressure difference of more than 150 kPa, the structure of the organic polymer membrane is highly likely to be destroyed, and therefore the capacity to produce a chemical product may be deteriorated. When the transmembrane pressure difference is less than 0.1 kPa, a sufficient amount of permeate of the fermentation culture liquid may not be obtained, and the productivity in production of the chemical product tends to be low. Accordingly, when an organic polymer membrane is used in the method of producing a chemical product, the transmembrane pressure difference, which is the filtration pressure, is preferably 0.1 kPa to 150 kPa since, in such a case, the amount of permeate of the fermentation culture liquid can be large, and the decrease in the capacity to produce a chemical product due to destruction of the membrane structure does not occur. Therefore, the capacity to produce a chemical product can be kept high in such a case. In cases of an organic polymer membrane, the transmembrane pressure difference is more preferably 0.1 kPa to 50 kPa, still more preferably 0.1 kPa to 20 kPa.

Also when a ceramic membrane is used, the transmembrane pressure difference during filtration is not limited as long as the fermentation culture liquid can be filtered. The transmembrane pressure difference is preferably not more than 500 kPa. When the operation is carried out at not less than 500 kPa, clogging of the membrane may occur to cause a trouble in the operation of continuous fermentation.

In terms of the driving force for the filtration, a siphon using the liquid level difference (hydraulic head difference) between the fermentation culture liquid and the liquid processed through the porous membrane, or a cross-flow circulating pump, may be used to generate the transmembrane pressure difference in the separation membrane. Further, as the driving force for the filtration, a suction pump may be placed in the secondary side of the separation membrane. When a cross-flow circulating pump is used, the transmembrane pressure difference can be controlled by the suction pressure. The transmembrane pressure difference can also be controlled by the pressure of the gas or liquid which is used to introduce the pressure into the fermentation liquid side. When such pressure control is carried out, the difference between the pressure in the fermentation liquid side and the pressure in the side of the liquid processed through the porous membrane can be regarded as the transmembrane pressure difference, and can be used to control the transmembrane pressure difference.

The concentration of pentose in the total amount of filtrate that has passed through the separation membrane is preferably kept at not more than 5 g/l. When continuous fermentation by a microorganism(s) that undergo(es) catabolite repression is carried out using a fermentation feedstock containing a mixed sugar of hexose and pentose, the culture medium is continuously utilized for the fermentation. Therefore, the microorganism(s) undergo(es) catabolite repression more continuously than in cases of batch fermentation. As a result, only pentose remains in a large amount in the culture liquid, and the production yield decreases. By using a separation membrane in continuous fermentation, the pentose concentration in the total amount of filtrate can be kept at not more than 5 g/l even in cases where a microorganism(s) that undergo(es) catabolite repression is/are used. As a result, the production yield of the chemical product can be increased compared to continuous fermentation without using a separation membrane. When pentose remains at not less than 5 g/l in the total amount of filtrate obtained by using a separation membrane, the effect of increasing the yield from pentose may decrease, resulting in a decreased production yield. The production yield herein means the production yield in continuous fermentation, and is calculated according to Equation 3 below, wherein the amount of the chemical product (g) produced by consumption of a carbon source material during a certain period is divided by the amount of the carbon source fed (g) during the period. In this calculation, the sugar that was not utilized for production of the product is also included in the amount of the carbon source fed.

Production yield (g/g)=Amount of product (g)/Amount of carbon source fed (g) (3)

The concentration of pentose in the total amount of filtrate can be controlled by culture conditions. For example, by changing the sugar concentration in the fermentation feedstock, the sugar supply rate and/or the dilution rate, the concentration of pentose in the total amount of filtrate can be reduced. Alternatively, by increasing a nutrient(s) contained in the fermentation feedstock, consumption of sugar by the microorganism(s) can be increased, and the concentration of pentose in the total amount of filtrate can be reduced.

The pH and the temperature during fermentation culture of the microorganism(s) are not limited as long as they are within the ranges in which the microorganism(s) can grow. The culture is preferably carried out at a pH of 4 to 8 and a temperature of 20 to 75° C. The pH of the culture liquid is adjusted in advance with an inorganic or organic acid, alkaline substance, urea, calcium carbonate, ammonia gas or the like to a predetermined pH of, usually, 4 to 8. When the feed rate of oxygen needs to be increased, the feed rate may be increased by, for example, maintaining the oxygen concentration at not less than 21% by adding oxygen into the air, pressurizing the culture liquid, increasing the stirring rate, and/or increasing the aeration rate.

Continuous fermentation (filtration of culture liquid) may be started after increasing the microorganism concentration by performing batch culture or fed-batch culture at an early stage of culture. Alternatively, microorganism cells may be seeded at high concentration, and continuous fermentation may then be carried out from the beginning of the culture. Supply of the culture medium and filtration of the culture liquid may be carried out from an appropriate timing(s). The timings of beginning of the supply of the culture medium and filtration of the culture liquid do not necessarily need to be the same. The supply of the culture medium and filtration of the culture liquid may be carried out either continuously or intermittently.

A nutrient(s) necessary for growth of the microorganism cells may be added to the raw culture liquid to allow continuous growth of the cells. The microorganism concentration in the culture liquid is preferably maintained such that the productivity of the chemical product is kept high to obtain efficient productivity. A good production efficiency can be obtained by maintaining the microorganism concentration in the culture liquid at, for example, not less than 5 g/L in terms of the dry weight.

If necessary, during the continuous fermentation in the method of producing a chemical product, the microorganism concentration in the culture vessel may be controlled by removing a part of the culture liquid containing the microorganism(s) from the fermenter and then diluting the culture liquid in the vessel with a culture medium. For example, when the microorganism concentration in the fermenter is too high, clogging of the separation membrane is likely to occur. Clogging may be avoided by removing a part of the culture liquid containing the microorganism(s) and then diluting the culture liquid in the fermenter with the culture medium. Further, the performance of producing the chemical product may change depending on the microorganism concentration in the fermenter. The production performance may be maintained by removing a part of the culture liquid containing the microorganism(s) and then diluting the culture liquid in the fermenter with a culture medium, using the production performance as an index.

The number of fermenters is not limited as long as the continuous fermentation culture is carried out by growing microorganism cells while allowing the cells to produce the product.

A higher production rate per volume can be obtained compared to conventional batch fermentation and, therefore, very efficient continuous fermentation production is possible. The production rate in the continuous fermentation culture herein can be calculated according to Equation (4) below:

Fermentation production rate (g/L/hr)=Concentration of product in filtrate (g/L)×Rate of removal of fermentation culture liquid (L/hr)/Operational liquid volume of apparatus (L) (4).

The fermentation production rate in batch culture can be determined by dividing the amount of the product (g) upon complete consumption of the carbon source in the feedstock by the time (hr) required for the consumption of the carbon source and the volume (L) of the fermentation culture liquid at that time.

The yield in the continuous culture can be calculated according to Equation (5) below by dividing the amount of chemical product (g) produced by consumption of the carbon source in the feedstock during a predetermined period by the value obtained by subtracting the amount of carbon source unused by the microorganism(s) (g) from the amount of carbon source fed (g) during this period. The yield means this unless otherwise specified.

Yield (g/g)=Amount of product (g)/{Amount of carbon source fed (g)−Amount of unused carbon source (g)} ( )

The continuous fermentation apparatus is not limited as long as it is an apparatus that produces a chemical product by continuous fermentation in which a fermentation culture liquid of a microorganism(s) is filtered through a separation membrane and the product is recovered from the filtrate, while the unfiltered liquid is retained in, or refluxed to, the fermentation culture liquid; a fermentation feedstock is added to the fermentation culture liquid; and the product in the filtrate is recovered. Specific examples of the apparatus in which an organic polymer membrane is used include the apparatus described in WO 2007/097260. Specific examples of the apparatus in which a ceramic membrane is used include the apparatus described in WO 2012/086763.

Next, the microorganism(s) that may be used in our methods is explained below.

The microorganism that undergoes catabolite repression generally means a microorganism which metabolizes pentose and whose consumption of pentose is suppressed when fermentation is carried out with a fermentation feedstock comprising a mixed sugar containing hexose and pentose. More specifically, "a microorganism that undergoes catabolite repression" refers to a microorganism which is capable of metabolizing glucose and xylose and whose consumption of xylose is slower in a culture medium comprising a mixed sugar containing glucose and xylose than in a culture medium containing xylose alone when it is cultured by batch culture.

The rate of consumption of xylose in a culture medium containing xylose alone is calculated according to Equation 6 below:

Xylose consumption rate (g/L/hr)=Total amount of xylose (g) contained in the fermentation feedstock at the beginning of culture/Time (hr) required for complete consumption of the xylose contained in the fermentation feedstock after the beginning of culture/Amount of fermentation liquid (L) (6).

The rate of consumption of xylose in a culture medium comprising a mixed sugar containing glucose and xylose means the rate of consumption of xylose in the presence of glucose in a culture medium comprising a mixed sugar containing glucose and xylose, and is calculated according to Equation 7 below:

Xylose consumption rate (g/L/hr)=Amount of xylose (g) consumed from the beginning of culture to the time T/Length of time (hr) from the beginning of culture to the time T/Amount of fermentation liquid (L) (7).

In calculation of the xylose consumption rates in Equations 6 and 7, the weight ratio between glucose and xylose in the mixed sugar is set as 1:1. In comparison of the xylose consumption rates, the sugar concentration is not limited as long as the sugar can be completely consumed by the microorganism without leaving residual sugar. The sugar concentration in the culture medium containing xylose alone is set as the same as the total sugar concentration in the culture medium containing the mixed sugar containing glucose and xylose.

In Equation 7, the time T is the time when glucose has been completely consumed. The time T can be determined by measuring the glucose concentration in sampled culture liquid by HPLC, or using a kit or sensor. When complete consumption of glucose occurred later than complete consumption of xylose, the time T is defined as the time when xylose was completely consumed. Also, in such cases, the time T can be determined by measuring the xylose concentration in the same manner as in the method of measuring the glucose concentration. When the amount of fermentation liquid has changed by addition of a neutralizer or by sampling during the culture, the calculation is carried out in consideration of the amount of liquid added to the culture liquid or the amount of liquid decreased.

The microorganism that undergoes catabolite repression is selected from yeasts such as baker's yeast; bacteria such as *E. coli* and corynebacteria; filamentous fungi; actinomycetes; and the like; which are often used in the fermentation industry. Specific examples of microorganisms that may be selected include yeasts such as *Pichia, Candida, Pachysolen, Kluyveromyces, Hansenula, Torulopsis, Debaryomyces, Issachenkia, Brettanomyces, Lindnera* and *Wickerhamomyces*; enterobacteria such as *Clostridium, Enterobacter, Escherichia* and *Klebsiella*; lactic acid bacteria such as *Lactobacillus* and *Lactococcus*; actinomycetes such as *Actinoplanes, Arthrobacter* and *Streptomyces*; and microorganisms belonging to *Bacillus, Paenibacillus, Aerobacter, Ampullariella, Staphylococcus, Thermoanaerobacter* or *Thermus*.

The microorganism(s) that undergo(es) catabolite repression may be selected either from microorganisms isolated from the natural environment or from microorganisms that do not originally metabolize pentose but are modified by mutation or genetic recombination such that they metabolize pentose. Specific examples of the microorganisms that are modified by genetic recombination such that they metabolize pentose include microorganisms in which a metabolic gene for pentose is introduced or enhanced by genetic recombination. Specific examples of metabolic genes for xylose among pentoses include the genes for enzymes such as xylose isomerase, xylose reductase, xylitol dehydrogenase and xylulose kinase, and examples of microorganisms given a xylose metabolic capacity by such genetic recombination include microorganisms described in JP 2006-525029 A, JP 2009-112289 A and JP 2010-504756 A.

The chemical product is not restricted as long as it is a substance produced in a fermentation culture liquid by the above-described microorganisms. Examples of the chemical product include alcohols, organic acids, amino acids and nucleic acids, which are substances mass-produced in the fermentation industry. Examples the substances include alcohols such as ethanol, 1,3-propanediol, 1,3-butanediol, 2,3-butanediol, 1,4-butanediol, glycerol, butanol, isobutanol, 2-butanol and isopropanol; organic acids such as acetic acid, lactic acid, adipic acid, pyruvic acid, succinic acid, malic acid, itaconic acid and citric acid; nucleic acids such as nucleosides including inosine and guanosine, and nucleotides including inosinic acid and guanylic acid; and diamine compounds such as cadaverine. Further, our methods may also be applied to production of substances such as enzymes, antibiotics and recombinant proteins. These chemical products can be recovered from the filtrate by well-known methods (membrane separation, concentration, distillation, crystallization, extraction and the like).

EXAMPLES

Our methods will now be described concretely by way of Examples. However, this disclosure is not limited to these.

Reference Example 1: Method of Analyzing Glucose, Xylose, Ethanol and 2,3-Butanediol The concentrations of glucose, xylose, ethanol and 2,3-butanediol in the fermentation liquid were quantified under the following HPLC conditions by comparison with standard samples:
Column: Shodex SH1011 (manufactured by Showa Denko K. K.)
Mobile phase: 5 mM sulfuric acid (flow rate: 0.6 mL/min)
Reaction liquid: none
Detection method: RI (differential refractive index)
Temperature: 65° C.

Reference Example 2: Method of Analyzing Lactic Acid

Lactic acid in the fermentation liquid was quantified under the following HPLC conditions by comparison with standard samples:
Column: Shim-Pack SPR-H (manufactured by Shimadzu Corporation)
Mobile phase: 5 mM p-toluenesulfonic acid (flow rate: 0.8 mL/min)
Reaction liquid: 5 mM p-toluenesulfonic acid, 20 mM Bis-Tris, 0.1 mM EDTA-2Na (flow rate: 0.8 mL/min)
Detection method: electric conductivity
Temperature: 45° C.

Reference Example 3: Calculation of Rate of Consumption of Xylose by *Bacillus coagulans*

The xylose consumption rate in lactic acid fermentation with a lactic acid fermentation microorganism, the *Bacillus coagulans* NBRC12714 strain, was calculated. As the culture medium, the lactic acid fermentation xylose medium having the composition shown in Table 1 or the lactic acid fermentation mixed-sugar medium 1 shown in Table 2 was used. Sampling was carried out as appropriate. The concentrations of glucose and xylose in the culture liquid were measured by the method of Reference Example 1, and the concentration of lactic acid as the product was measured by the method of Reference Example 2.

TABLE 1

| Lactic acid fermentation xylose medium | |
|---|---|
| Xylose | 100 g |
| Yeast extract | 5 g |
| Ammonium sulfate | 1 g |
| $K_2HPO_4$ | 0.4 g |

Unit (1/Liter)

TABLE 2

| Lactic acid fermentation mixed-sugar medium 1 | |
|---|---|
| Glucose | 50 g |
| Xylose | 50 g |

TABLE 2-continued

| Lactic acid fermentation mixed-sugar medium 1 | |
| --- | --- |
| Yeast extract | 5 g |
| Ammonium sulfate | 1 g |
| K₂HPO₄ | 0.4 g |

Unit (1/Liter)

The *Bacillus coagulans* NBRC12714 strain was cultured in 50 mL of a preculture medium (10 g/L polypeptone, 2 g/L yeast extract, 1 g/L magnesium sulfate 7H₂O) supplemented with calcium carbonate in a flask for 24 hours with shaking (preculture). The preculture liquid was inoculated to 1 L of the lactic acid fermentation xylose medium or the lactic acid fermentation mixed-sugar medium 1 purged with nitrogen gas, and batch fermentation was performed under the following conditions:
  Fermentation reaction vessel capacity: 2 (L)
  Temperature adjustment: 50 (° C.)
  Aeration in the reaction vessel (nitrogen gas): 100 (mL/min)
  Stirring rate in the reaction vessel: 200 (rpm)
  pH Adjustment: adjusted to pH 7 with 5 N Ca(OH)₂
  Sterilization: the culture vessels and media to be used were all subjected to high-pressure steam sterilization by autoclaving at 121° C. for 20 min.

The xylose consumption rates in the lactic acid fermentation xylose medium and the lactic acid fermentation mixed-sugar medium 1 were calculated according to Equations 6 and 7 described above, respectively. The calculation results are shown in Table 7. From these results, the *Bacillus coagulans* NBRC12714 strain was judged to be a microorganism that undergoes catabolite repression.

Reference Example 4: Calculation of Rate of Consumption of Xylose by *Candida tropicalis*

The xylose consumption rate in ethanol fermentation with an ethanol fermentation microorganism, the *Candida tropicalis* NBRC0199 strain, was calculated. As the culture medium, the ethanol fermentation xylose medium having the composition shown in Table 3 or the ethanol fermentation mixed-sugar medium 1 shown in Table 4 was used. Sampling was carried out as appropriate. The concentrations of glucose and xylose in the culture liquid, and the concentration of ethanol as the product were measured by the method of Reference Example 1.

TABLE 3

| Ethanol fermentation xylose medium | |
| --- | --- |
| Xylose | 100 g |
| Peptone | 20 g |
| Yeast extract | 10 g |

Unit (1/Liter)

TABLE 4

| Ethanol fermentation mixed-sugar medium 1 | |
| --- | --- |
| Glucose | 50 g |
| Xylose | 50 g |
| Peptone | 20 g |
| Yeast extract | 10 g |

Unit (1/Liter)

The *Candida tropicalis* NBRC0199 strain was cultured in 2 mL of YPD medium in a test tube at 30° C. overnight with shaking (pre-preculture). The obtained culture liquid was inoculated to 50 mL of fresh YPD medium, and culture was performed overnight with shaking in a 500-mL baffled Erlenmeyer flask (preculture). The preculture liquid was inoculated to 2 L of the ethanol fermentation xylose medium or the ethanol fermentation mixed-sugar medium, and batch culture was performed under the following conditions:
  Fermentation reaction vessel capacity: 2 (L)
  Temperature adjustment: 30 (° C.)
  Aeration in the reaction vessel: 100 (mL/min)
  Stirring rate in the reaction vessel: 800 (rpm)
  pH Adjustment: none
  Sterilization: the culture vessels and media to be used were all subjected to high-pressure steam sterilization by autoclaving at 121° C. for 20 min.

The xylose consumption rates in the ethanol fermentation xylose medium and the ethanol fermentation mixed-sugar medium 1 were calculated according to Equations 6 and 7 described above, respectively. The calculation results are shown in Table 7. From these results, the *Candida tropicalis* NBRC0199 strain was judged to be a microorganism that undergoes catabolite repression.

Reference Example 5: Calculation of Rate of Consumption of Xylose by *Paenibacillus polymyxa*

The xylose consumption rate in 2,3-butanediol fermentation with a 2,3-butanediol fermentation microorganism, the *Paenibacillus polymyxa* ATCC12321 strain, was calculated. As the culture medium, the 2,3-butanediol fermentation xylose medium having the composition shown in Table 5 or the 2,3-butanediol fermentation mixed-sugar medium 1 shown in Table 6 was used. Sampling was carried out as appropriate, and the concentrations of glucose and xylose in the culture liquid, and the concentration of 2,3-butanediol as the product were measured by the method of Reference Example 1.

TABLE 5

| 2,3-Butanediol fermentation xylose medium | |
| --- | --- |
| Xylose | 60 g |
| Yeast extract | 13.1 g |
| Ammonium sulfate | 5.8 g |
| KH₂PO₄ | 1.75 g |
| K₂HPO₄ | 9.2 g |
| (NH₄)₂HPO₄ | 2.9 g |
| CaCl₂•2H₂O | 8.8 mg |
| FeSO₄•7H₂O | 44 mg |
| MnSO₄•5H₂O | 1.28 mg |
| ZnSO₄•7H₂O | 0.9 mg |
| MgSO₄•7H₂O | 219 mg |
| EDTA•2Na | 44 mg |

Unit (1/Liter)

TABLE 6

| 2,3-Butanediol fermentation mixed-sugar medium 1 | |
| --- | --- |
| Glucose | 30 g |
| Xylose | 30 g |
| Yeast extract | 13.1 g |
| Ammonium sulfate | 5.8 g |
| KH₂PO₄ | 1.75 g |
| K₂HPO₄ | 9.2 g |
| (NH₄)₂HPO₄ | 2.9 g |
| CaCl₂•2H₂O | 8.8 mg |

TABLE 6-continued

| 2,3-Butanediol fermentation mixed-sugar medium 1 | |
|---|---|
| FeSO$_4$•7H$_2$O | 44 mg |
| MnSO$_4$•5H$_2$O | 1.28 mg |
| ZnSO$_4$•7H$_2$O | 0.9 mg |
| MgSO$_4$•7H$_2$O | 219 mg |
| EDTA•2Na | 44 mg |

Unit (1/Liter)

The *Paenibacillus polymyxa* ATCC12321 strain was cultured in 50 mL of a preculture medium (5 g/L glucose, 5 g/L peptone, 3 g/L yeast extract, 3 g/L malt extract) in a test tube with shaking for 24 hours (preculture). The preculture liquid was inoculated to 1 L of the 2,3-butanediol fermentation xylose medium or the 2,3-butanediol fermentation mixed-sugar medium, and batch culture was performed under the following conditions:
Fermentation reaction vessel capacity: 2 (L)
Temperature adjustment: 30 (° C.)
Aeration in the reaction vessel: 100 (mL/min)
Stirring rate in the reaction vessel: 800 (rpm)
pH Adjustment: adjusted to pH 6.5 with 5 N NaOH
Sterilization: the culture vessels and media to be used were all subjected to high-pressure steam sterilization by autoclaving at 121° C. for 20 min.

The xylose consumption rates in the 2,3-butanediol fermentation xylose medium and the 2,3-butanediol fermentation mixed-sugar medium 1 were calculated according to Equations 6 and 7 described above, respectively. The calculation results are shown in Table 7. From these results, the *Paenibacillus polymyxa* ATCC12321 strain was judged to be a microorganism that undergoes catabolite repression.

TABLE 7

| | (Reference Example 3) | (Reference Example 4) | (Reference Example 5) |
|---|---|---|---|
| Xylose consumption rate in the xylose medium (g/L/hr) | 0.78 | 2.70 | 0.82 |
| Xylose consumption rate in the mixed-sugar medium (g/L/hr) | 0.33 | 0.48 | 0.08 |

Comparative Example 1: Production of L-Lactic Acid by Batch Culture of *Bacillus coagulans* Using Hexose (Glucose) as Fermentation Feedstock As an L-lactic acid fermentation microorganism, the *Bacillus coagulans* NBRC12714 strain was used, and, as a culture medium, the lactic acid fermentation medium having the composition shown in Table 8 was used. The *Bacillus coagulans* NBRC12714 strain was cultured in 50 mL of a preculture medium (10 g/L polypeptone, 2 g/L yeast extract, 1 g/L magnesium sulfate 7H$_2$O) supplemented with calcium carbonate in a flask for 24 hours with shaking (preculture). The preculture liquid was inoculated to 1 L of the lactic acid fermentation medium purged with nitrogen gas, and batch culture was performed for 96 hours under the conditions of Reference Example 3 (Table 11).

TABLE 8

| Lactic acid fermentation medium | |
|---|---|
| Glucose | 100 g |
| Yeast extract | 5 g |

TABLE 8-continued

| Lactic acid fermentation medium | |
|---|---|
| Ammonium sulfate | 1 g |
| K$_2$HPO$_4$ | 0.4 g |

Unit (1/Liter)

Comparative Example 2: Production of L-Lactic Acid by Batch Culture of *Bacillus coagulans* Using Mixed Sugar (Glucose, Xylose) as Fermentation Feedstock The *Bacillus coagulans* NBRC12714 strain was subjected to batch culture for 128 hours using the lactic acid fermentation mixed-sugar medium shown in Table 2 under the same conditions as in Comparative Example 1 (Table 11).

Comparative Example 3: Production of L-Lactic Acid by Continuous Culture of *Bacillus coagulans* Using Mixed Sugar (Glucose, Xylose) as Fermentation Feedstock Using a mixed sugar (glucose, xylose) as the fermentation feedstock, continuous culture was carried out with the lactic acid fermentation mixed-sugar medium 1 having the composition shown in Table 2 without using a separation membrane. The *Bacillus coagulans* NBRC12714 strain was cultured with shaking under the same conditions as in the preculture in Comparative Example 1 (pre-preculture). The pre-preculture liquid was inoculated to 1.5 L of the lactic acid fermentation mixed-sugar medium purged with nitrogen gas. In a fermentation reaction vessel filled with nitrogen, batch culture was performed with stirring at 200 rpm by the stirrer attached to the fermentation reaction vessel while the temperature was controlled, until complete consumption of the sugar in the culture liquid (preculture). Immediately after completion of the preculture, after completion of the preculture, operation of a pump for collecting the fermentation liquid was immediately started, and the culture medium was continuously supplied. While the amount of collection of culture liquid containing the microorganism was controlled such that the amount of fermentation liquid in the continuous fermentation apparatus was 1.5 L, continuous culture was performed for 300 hours under the following conditions to produce lactic acid (Table 11):
Fermentation reaction vessel capacity: 2 (L)
Temperature adjustment: 50 (° C.)
Aeration in the reaction vessel (nitrogen gas): 100 (mL/min)
Stirring rate in the reaction vessel: 200 (rpm)
pH Adjustment: adjusted to pH 7 with 5 N Ca(OH)$_2$
Amount of the fermentation liquid collected: 3 (L/day)
Sterilization: the culture vessels and media to be used were all subjected to high-pressure steam sterilization by autoclaving at 121° C. for 20 min.

Example 1: Production of L-Lactic Acid by Continuous Culture of *Bacillus coagulans* Using Mixed Sugar (Glucose, Xylose) as Fermentation Feedstock, with Use of Separation Membrane 1

Using a mixed sugar (glucose, xylose) as the fermentation feedstock, continuous culture was carried out with the lactic acid fermentation mixed-sugar medium having the composition shown in Table 2 using a separation membrane. The separation membrane element employed was in a hollow-fiber shape. The *Bacillus coagulans* NBRC12714 strain was cultured with shaking under the same conditions as in the preculture in Comparative Example 1 (pre-preculture). The pre-preculture liquid was inoculated to 1.5 L of the lactic acid fermentation mixed-sugar medium purged with nitrogen gas. In a fermentation reaction vessel filled with nitrogen, batch culture was performed with stirring at 200 rpm by the stirrer attached to the fermentation reaction vessel while the temperature was controlled, until complete consumption of the sugar in the culture liquid (preculture). Immediately after completion of the preculture, operation of a pump to circulate the fermentation liquid was started, and the culture medium was continuously supplied. While the amount of culture liquid filtered was controlled such that the amount of fermentation liquid in the continuous fermentation apparatus was 1.5 L, continuous culture was performed for 290 hours under the following conditions to produce lactic acid (Table 11):

Fermentation reaction vessel capacity: 2 (L)
Separation membrane used: polyvinylidene fluoride filtration membrane
Effective filtration area of the membrane separation element: 473 ($cm^2$)
Temperature adjustment: 50 (° C.)
Aeration in the fermentation reaction vessel (nitrogen gas): 100 (mL/min)
Stirring rate in the fermentation reaction vessel: 200 (rpm)
Amount of the fermentation liquid collected: 3 (L/day)
Sterilization: the culture vessels comprising the separation membrane element, and the culture media to be used were all subjected to high-pressure steam sterilization by autoclaving at 121° C. for 20 min.

The membrane used was a membrane having the following properties, and the transmembrane pressure difference during filtration was allowed to change within the range of 0.1 to 20 kPa:

Average pore size: 0.1 μm
Standard deviation of the average pore size: 0.035 μm
Membrane surface roughness: 0.06 μm
Pure water permeation coefficient: $50 \times 10^{-9}$ $m^3/m^2/s/pa$.

Example 2: Continuous Culture of *Bacillus coagulans* Using Mixed Sugar (Glucose, Xylose) as Fermentation Feedstock, with Use of Separation Membrane 2

Using the lactic acid fermentation mixed-sugar medium 2 shown in Table 9, continuous culture was carried out for 305 hours with use of a separation membrane under the same conditions as in Example 1 to produce L-lactic acid (Table 11).

TABLE 9

| Lactic acid fermentation mixed-sugar medium 2 | |
| --- | --- |
| Glucose | 80 g |
| Xylose | 20 g |
| Yeast extract | 5 g |
| Ammonium sulfate | 1 g |
| $K_2HPO_4$ | 0.4 g |

Unit (1/Liter)

Example 3: Continuous Culture of *Bacillus coagulans* Using Mixed Sugar (Glucose, Xylose) as Fermentation Feedstock, with Use of Separation Membrane 3

Using the lactic acid fermentation mixed-sugar medium 3 shown in Table 10, continuous culture was carried out for 300 hours with use of a separation membrane under the same conditions as in Example 1 to produce L-lactic acid (Table 11).

TABLE 10

| Lactic acid fermentation mixed-sugar medium 3 | |
| --- | --- |
| Glucose | 20 g |
| Xylose | 80 g |
| Yeast extract | 5 g |
| Ammonium sulfate | 1 g |
| $K_2HPO_4$ | 0.4 g |

Unit (1/Liter)

TABLE 11

| | (Comparative Example 1) | (Comparative Example 2) | (Comparative Example 3) | (Example 1) | (Example 2) | (Example 3) |
| --- | --- | --- | --- | --- | --- | --- |
| Fermentation period (hr) | 96 | 128 | 300 | 290 | 305 | 300 |
| Total glucose fed (g) | 100 | 50 | 1870 | 1810 | 3050 | 750 |
| Total xylose fed (g) | 0 | 50 | 1870 | 1810 | 760 | 3000 |
| Total production of lactic acid (g) | 75 | 66 | 1700 | 3040 | 3180 | 3150 |
| Unused glucose (g) | 0 | 0 | 0 | 0 | 0 | 0 |
| Unused xylose (g) | 0 | 0 | 1310 | 35 | 40 | 40 |
| Unused xylose/ total amount of filtrate (g/L) | 0 | 0 | 35 | 1 | 1 | 1 |
| Yield (g/g) | 0.75 | 0.66 | 0.70 | 0.85 | 0.84 | 0.85 |

Comparative Example 4: Production of Ethanol by Batch Culture of *Candida tropicalis* Using Hexose (Glucose) as Fermentation Feedstock The *Candida tropicalis* NBRC0199 strain was used as an ethanol fermentation microorganism, and the ethanol fermentation medium having the composition shown in Table 12 was used as the culture medium. The *Candida tropicalis* NBRC0199 strain was cultured in 2 mL of YPD medium in a test tube at 30° C. overnight with shaking (pre-preculture). The obtained culture liquid was inoculated to 50 mL of fresh YPD medium, and culture was performed overnight with shaking in a 500-mL baffled Erlenmeyer flask (preculture). The preculture liquid was inoculated to 1.5 L of the ethanol fermentation medium, and batch culture was performed for 16 hours under the following conditions to produce ethanol (Table 14):
- Fermentation reaction vessel capacity: 2 (L)
- Temperature adjustment: 30 (° C.)
- Aeration in the reaction vessel: 100 (mL/min)
- Stirring rate in the reaction vessel: 800 (rpm)
- pH Adjustment: none
- Sterilization: the culture vessels and media to be used were all subjected to high-pressure steam sterilization by autoclaving at 121° C. for 20 min.

TABLE 12

| Ethanol fermentation medium | |
| --- | --- |
| Glucose | 70 g |
| Peptone | 20 g |
| Yeast extract | 10 g |

Unit (1/Liter)

Comparative Example 5: Production of Ethanol by Batch Culture of *Candida tropicalis* Using Mixed Sugar (Glucose, Xylose) as Fermentation Feedstock Using the ethanol fermentation mixed-sugar medium 2 shown in Table 13, batch culture was carried out for 23 hours under the same conditions as in Comparative Example 4 to produce ethanol (Table 14).

TABLE 13

| Ethanol fermentation mixed-sugar medium 2 | |
| --- | --- |
| Glucose | 30 g |
| Xylose | 40 g |
| Peptone | 20 g |
| Yeast extract | 10 g |

Unit (1/Liter)

Comparative Example 6: Production of Ethanol by Continuous Culture of *Candida tropicalis* Using Mixed Sugar as Fermentation Feedstock Using the ethanol fermentation mixed-sugar medium 2 shown in Table 13 as the culture medium, continuous fermentation was carried out without using a separation membrane. The *Candida tropicalis* NBRC0199 strain was cultured in 2 mL of YPD medium in a test tube at 30° C. overnight with shaking (pre-pre-preculture). The obtained culture liquid was inoculated to 50 mL of fresh YPD medium, and culture was performed overnight with shaking in a 500-mL baffled Erlenmeyer flask (pre-preculture). The pre-preculture liquid was inoculated to 1.5 L of the ethanol fermentation mixed-sugar medium 2 in a continuous fermentation apparatus, and culture was carried out for 16 hours with stirring at 800 rpm by the stirrer attached to the fermentation reaction vessel while the aeration rate and the temperature in the fermentation reaction vessel were controlled (preculture). Immediately after completion of the preculture, operation of a pump collect the fermentation liquid was started, and the culture medium was continuously supplied. While the amount of collection of culture liquid containing the microorganism was controlled such that the amount of fermentation liquid in the continuous fermentation apparatus was 1.5 L, continuous culture was performed for 295 hours under the following conditions to produce ethanol (Table 14):
- Fermentation reaction vessel capacity: 2 (L)
- Temperature adjustment: 30 (° C.)
- Aeration in the fermentation reaction vessel: 100 (mL/min)
- Stirring rate in the fermentation reaction vessel: 800 (rpm)
- pH Adjustment: none
- Amount of the fermentation liquid collected: 1 (L/day)
- Sterilization: the culture vessels and media to be used were all subjected to high-pressure steam sterilization by autoclaving at 121° C. for 20 min.

Example 4: Production of Ethanol by Continuous Culture of *Candida tropicalis* Using Mixed Sugar (Glucose, Xylose) as Fermentation Feedstock, with Use of Separation Membrane Using the ethanol fermentation mixed-sugar medium 2 having the composition shown in Table 13 as the culture medium, continuous fermentation was carried out with use of a separation membrane. The separation membrane element employed was in a flat-membrane shape. The *Candida tropicalis* NBRC0199 strain was cultured in 2 mL of YPD medium in a test tube at 30° C. overnight (pre-pre-preculture). The obtained culture liquid was inoculated to 50 mL of fresh YPD medium, and culture was performed overnight with shaking in a 500-mL baffled Erlenmeyer flask (pre-preculture). The pre-preculture liquid was inoculated to 1.5 L of the ethanol fermentation mixed-sugar medium 2 in a continuous fermentation apparatus, and culture was carried out for 36 hours with stirring at 800 rpm by the stirrer attached to the fermentation reaction vessel while the aeration rate and the temperature in the fermentation reaction vessel were controlled (preculture). Immediately after completion of the preculture, operation of a pump to circulate the fermentation liquid was started, and the culture medium was continuously supplied. While the amount of culture liquid filtered was controlled such that the amount of fermentation liquid in the continuous fermentation apparatus was 1.5 L, continuous culture was performed for 300 hours under the following conditions to produce ethanol (Table 14):
- Fermentation reaction vessel capacity: 2 (L)
- Separation membrane used: polyvinylidene fluoride filtration membrane
- Effective filtration area of the membrane separation element: 120 (cm$^2$)
- Temperature adjustment: 30 (° C.)
- Aeration in the fermentation reaction vessel: 100 (mL/min)
- Stirring rate in the fermentation reaction vessel: 800 (rpm)
- pH Adjustment: none
- Amount of the fermentation liquid collected: 1 (L/day)
- Sterilization: the culture vessels comprising the separation membrane element, and the culture media to be used were all subjected to high-pressure steam sterilization by autoclaving at 121° C. for 20 min.

The membrane used was a membrane having the same properties as in Example 1, and the transmembrane pressure difference during filtration was allowed to change within the range of 0.1 to 19.8 kPa.

TABLE 14

|  | (Comparative Example 4) | (Comparative Example 5) | (Comparative Example 6) | (Example 4) |
|---|---|---|---|---|
| Fermentation period (hr) | 16 | 23 | 295 | 300 |
| Total glucose fed (g) | 70 | 30 | 370 | 375 |
| Total xylose fed (g) | 0 | 40 | 490 | 500 |
| Total production of ethanol (g) | 32 | 17 | 215 | 290 |
| Unused glucose (g) | 0 | 0 | 0 | 0 |
| Unused xylose (g) | 0 | 0 | 50 | 13 |
| Unused xylose/total amount of filtrate (g/L) | 0 | 0 | 4 | 1 |
| Yield (g/g) | 0.46 | 0.24 | 0.27 | 0.34 |

Comparative Example 7: Production of 2,3-Butanediol by Batch Culture of *Paenibacillus polymyxa* Using Hexose (Glucose) as Fermentation Feedstock The *Paenibacillus polymyxa* ATCC12321 strain, which is a 2,3-butanediol microorganism, and the 2,3-butanediol fermentation medium having the composition shown in Table 15 as the culture medium, were used.

TABLE 15

| 2,3-Butanediol fermentation medium | |
|---|---|
| Glucose | 60 g |
| Yeast extract | 13.1 g |
| Ammonium sulfate | 5.8 g |
| $KH_2PO_4$ | 1.75 g |
| $K_2HPO_4$ | 9.2 g |
| $(NH_4)_2HPO_4$ | 2.9 g |
| $CaCl_2 \cdot 2H_2O$ | 8.8 mg |
| $FeSO_4 \cdot 7H_2O$ | 44 mg |
| $MnSO_4 \cdot 5H_2O$ | 1.28 mg |
| $ZnSO_4 \cdot 7H_2O$ | 0.9 mg |
| $MgSO_4 \cdot 7H_2O$ | 219 mg |
| $EDTA \cdot 2Na$ | 44 mg |

Unit (1/Liter)

The *Paenibacillus polymyxa* ATCC12321 strain was cultured in 50 mL of a preculture medium (5 g/L glucose, 5 g/L peptone, 3 g/L yeast extract, 3 g/L malt extract) in a test tube with shaking for 24 hours (preculture). The preculture liquid was inoculated to 1 L of the 2,3-butanediol fermentation medium, and batch culture was performed under the following conditions for 27 hours to produce 2,3-butanediol (Table 17):
Fermentation reaction vessel capacity: 2 (L)
Temperature adjustment: 30 (° C.)
Aeration in the reaction vessel: 100 (mL/min)
Stirring rate in the reaction vessel: 800 (rpm)
pH Adjustment: adjusted to pH 6.5 with 5 N NaOH
Sterilization: the culture vessels and media to be used were all subjected to high-pressure steam sterilization by autoclaving at 121° C. for 20 min.

Comparative Example 8: Production of 2,3-Butanediol by Batch Culture of *Paenibacillus polymyxa* Using Mixed Sugar (Glucose, Xylose) as Fermentation Feedstock Using the mixed-sugar 2,3-butanediol fermentation medium 2 shown in Table 16, batch culture was carried out under the same conditions as in Comparative Example 7 for 50 hours to produce 2,3-butanediol (Table 17).

TABLE 16

| 2,3-Butanediol fermentation mixed-sugar medium 2 | |
|---|---|
| Glucose | 20 g |
| Xylose | 40 g |
| Yeast extract | 13.1 g |
| Ammonium sulfate | 5.8 g |
| $KH_2PO_4$ | 1.75 g |
| $K_2HPO_4$ | 9.2 g |
| $(NH_4)_2HPO_4$ | 2.9 g |
| $CaCl_2 \cdot 2H_2O$ | 8.8 mg |
| $FeSO_4 \cdot 7H_2O$ | 44 mg |
| $MnSO_4 \cdot 5H_2O$ | 1.28 mg |
| $ZnSO_4 \cdot 7H_2O$ | 0.9 mg |
| $MgSO_4 \cdot 7H_2O$ | 219 mg |
| $EDTA \cdot 2Na$ | 44 mg |

Unit (1/Liter)

Comparative Example 9: Production of 2,3-Butanediol by Continuous Culture of *Paenibacillus polymyxa* Using Mixed Sugar (Glucose, Xylose) as Fermentation Feedstock Using a mixed sugar (glucose, xylose) as the fermentation feedstock, continuous culture was carried out without using a separation membrane. The *Paenibacillus polymyxa* ATCC12321 strain was cultured with shaking under the same conditions as in the preculture in Comparative Example 7 (pre-preculture). The pre-preculture liquid was inoculated to 1.2 L of the mixed-sugar 2,3-butanediol fermentation medium 2 shown in Table 16. Batch culture was performed in a fermentation reaction vessel with stirring at 200 rpm by the stirrer attached to the vessel while the temperature was controlled, until complete consumption of the sugar in the culture liquid (preculture). Immediately after completion of the preculture, after completion of the pre-culture, operation of a pump to collect the fermentation liquid was immediately started, and the culture medium was continuously supplied. While the amount of collection of culture liquid containing the microorganism was controlled such that the amount of fermentation liquid in the continuous fermentation apparatus was 1.2 L, continuous culture was performed for 280 hours under the following conditions to produce 2,3-butanediol (Table 17):
Fermentation reaction vessel capacity: 2 (L)
Temperature adjustment: 30 (° C.)
Aeration in the reaction vessel: 100 (mL/min)
Stirring rate in the reaction vessel: 800 (rpm)
pH Adjustment: adjusted to pH 6.5 with 5 N NaOH
Amount of the fermentation liquid collected: 0.6 (L/day)
Sterilization: the culture vessels and media to be used were all subjected to high-pressure steam sterilization by autoclaving at 121° C. for 20 min.

Example 5: Production of 2,3-Butanediol by Continuous Culture of *Paenibacillus polymyxa* Using Mixed Sugar (Glucose, Xylose) as Fermentation Feedstock, with Use of Separation Membrane Using a mixed sugar (glucose, xylose) as the fermentation feedstock, continuous culture was carried out with use of a separation membrane. The separation membrane element employed was in a flat-membrane shape. The *Paenibacillus polymyxa* ATCC12321 strain was cultured with shaking under the same conditions as in the preculture in Comparative Example 7 (pre-preculture). The pre-preculture liquid was inoculated to 1.2 L of the mixed-sugar 2,3-butanediol fermentation medium 2. Batch culture was performed in a fermentation reaction vessel with stirring at 200 rpm by the stirrer attached to the vessel while the temperature was controlled, until complete consumption of the sugar in the culture liquid (preculture). Immediately after completion of the preculture, operation of a pump to circulate the fermentation liquid was started, and the culture medium was continuously supplied. While the amount of culture liquid filtered was controlled such that the amount of fermentation liquid in the continuous fermentation apparatus was 1.2 L, continuous culture was performed for 310 hours under the following conditions to produce 2,3-butanediol (Table 17):

Fermentation reaction vessel capacity: 2 (L)
Separation membrane used: polyvinylidene fluoride filtration membrane
Effective filtration area of the membrane separation element: 120 (cm$^2$)
Temperature adjustment: 30 (° C.)
Aeration in the fermentation reaction vessel: 100 (mL/min)
Stirring rate in the fermentation reaction vessel: 800 (rpm)
Amount of the fermentation liquid collected: 0.6 L/day
Sterilization: the culture vessels comprising the separation membrane element, and the culture media to be used were all subjected to high-pressure steam sterilization by autoclaving at 121° C. for 20 min.

The membrane used was a membrane having the same properties as in Example 1, and the transmembrane pressure difference during filtration was allowed to change within the range of 0.1 to 20 kPa.

The xylose consumption rates in the ethanol fermentation xylose medium and the ethanol fermentation mixed-sugar medium 1 were calculated according to Equations 6 and 7 described above, respectively. The calculation results are shown in Table 22. From these results, the *Pichia stipitis* NBRC1687 strain was judged to be a microorganism that undergoes catabolite repression.

Reference Example 7: Calculation of Rate of Consumption of Xylose by *Candida utilis*

As the microorganism, the *Candida utilis* CuLpLDH strain, which was prepared by the method disclosed in WO 2010/140602, was used. As the culture medium, the D-lactic acid fermentation xylose medium having the composition shown in Table 18 or the D-lactic acid fermentation mixed-sugar medium 1 shown in Table 19 was used. Batch culture was performed for 40 hours under the same conditions as in Comparative Example 1 except that the pH was adjusted to 6.0 with 1 N calcium hydroxide, and the rate of consumption of xylose in D-lactic acid fermentation was calculated.

The xylose consumption rates in the D-lactic acid fermentation xylose medium and the D-lactic acid fermentation mixed-sugar medium 1 were calculated according to Equations 6 and 7 described above, respectively. The calculation results are shown in Table 22. From these results, the *Candida utilis* CuLpLDH strain was judged to be a microorganism that undergoes catabolite repression.

TABLE 18

| D-Lactic acid fermentation xylose medium | |
|---|---|
| Xylose | 100 g |
| Yeast extract | 10 g |
| Bactopeptone | 20 g |

Unit (1/Liter)

TABLE 17

| | (Comparative Example 7) | (Comparative Example 8) | (Comparative Example 9) | (Example 5) |
|---|---|---|---|---|
| Fermentation period (hr) | 27 | 50 | 280 | 310 |
| Total glucose fed (g) | 60 | 20 | 155 | 170 |
| Total xylose fed (g) | 0 | 40 | 305 | 340 |
| Total production of 2,3-butanediol (g) | 15 | 2 | 45 | 145 |
| Unused glucose (g) | 0 | 0 | 0 | 0 |
| Unused xylose (g) | 0 | 0 | 115 | 5 |
| Unused xylose/total amount of filtrate (g/L) | 0 | 0 | 15 | 0.6 |
| Yield (g/g) | 0.25 | 0.03 | 0.13 | 0.29 |

Reference Example 6: Calculation of Rate of Consumption of Xylose by *Pichia stipitis*

Batch fermentation was carried out under the same conditions as in Reference Example 4 using as the culture medium the ethanol fermentation xylose medium shown in Table 3 or the ethanol fermentation mixed-sugar medium 1 shown in Table 4 to calculate the rate of consumption of xylose by an ethanol fermentation microorganism, the *Pichia stipitis* NBRC1687 strain, in ethanol fermentation.

TABLE 19

| D-Lactic acid fermentation mixed-sugar medium 1 | |
|---|---|
| Glucose | 50 g |
| Xylose | 50 g |
| Yeast extract | 10 g |
| Bactopeptone | 20 g |

Unit (1/Liter)

Reference Example 8: Calculation of Rate of Consumption of Xylose by *Escherichia coli* KO11 Strain The xylose consumption rate in ethanol fermentation with an ethanol fermentation microorganism, the *Escherichia coli* KO11 strain, was calculated. As the culture medium, the ethanol fermentation xylose medium 2 having the composition shown in Table 20 or the ethanol fermentation mixed-sugar medium 3 shown in Table 21 was used. Sampling was carried out as appropriate, and the concentrations of glucose and xylose in the culture liquid, and the concentration of ethanol as the product were measured by the method of Reference Example 1.

TABLE 20

| Ethanol fermentation xylose medium 2 | |
| --- | --- |
| Xylose | 60 g |
| Yeast extract | 10 g |
| Tryptone | 5 g |
| NaCl | 5 g |

Unit (1/Liter)

TABLE 21

| Ethanol fermentation mixed-sugar medium 3 | |
| --- | --- |
| Glucose | 30 g |
| Xylose | 30 g |
| Yeast extract | 10 g |
| Tryptone | 5 g |
| NaCl | 5 g |

Unit (1/Liter)

The *Escherichia coli* KO11 strain was cultured in 2 mL of a preculture medium (20 g/L glucose, 10 g/L yeast extract, 5 g/L tryptone, 5 g/L NaCl) in a test tube at 30° C. overnight (pre-preculture). The obtained culture liquid was inoculated to 50 mL of a preculture medium placed in a 500-mL baffled Erlenmeyer flask, and culture was performed overnight (preculture). The preculture liquid was inoculated to 1.5 L of the ethanol fermentation xylose medium 2 or the ethanol fermentation mixed-sugar medium 3, and batch fermentation was carried out for 16 hours under the following operating conditions while the temperature and the pH were controlled:

Culture vessel capacity: 2 (L)

Temperature adjustment: 30 (° C.)

Aeration in the fermentation reaction vessel: 100 (mL/min)

Stirring rate in the fermentation reaction vessel: 800 (rpm)

pH Adjustment: adjusted to pH 6 with 5 N Ca(OH)$_2$

Sterilization: the fermentation vessel and media to be used were all subjected to high-pressure steam sterilization by autoclaving at 121° C. for 20 min.

The xylose consumption rates in the ethanol fermentation xylose medium 2 and the ethanol fermentation mixed-sugar medium 3 were calculated according to Equations 6 and 7 described above, respectively. The calculation results are shown in Table 22. From these results, the *Escherichia coli* KO11 strain was judged to be a microorganism that undergoes catabolite repression.

TABLE 22

| | (Reference Example 6) | (Reference Example 7) | (Reference Example 8) |
| --- | --- | --- | --- |
| Xylose consumption rate in the xylose medium (g/L/hr) | 2.22 | 1.59 | 1.46 |
| Xylose consumption rate in the mixed-sugar medium (g/L/hr) | 0.25 | 0.09 | 0.16 |

Comparative Example 10: Production of Ethanol by Batch Culture of *Pichia stipitis* Using Hexose as Fermentation Feedstock Using the *Pichia stipitis* NBRC1687 strain as the microorganism, batch culture was performed under the same conditions as in Comparative Example 4 for 23 hours to produce ethanol (Table 23).

Comparative Example 11: Production of Ethanol by Batch Culture of *Pichia stipitis* Using Mixed Sugar as Fermentation Feedstock Using the *Pichia stipitis* NBRC1687 strain as the microorganism, batch culture was performed under the same conditions as in Comparative Example 5 for 40 hours to produce ethanol (Table 23).

Comparative Example 12: Production of Ethanol by Continuous Fermentation by *Pichia stipitis* Using Mixed Sugar as Fermentation Feedstock Using the *Pichia stipitis* NBRC1687 strain as the microorganism, continuous fermentation was carried out using a mixed sugar feedstock, without use of a separation membrane. The continuous fermentation was performed for 298 hours under the same conditions as in Comparative Example 6 except that the period of preculture was 40 hours, to produce ethanol (Table 23).

Example 6: Production of Ethanol by Continuous Fermentation by *Pichia stipitis* Using Mixed Sugar as Fermentation Feedstock, with Use of Separation Membrane 1

Using the *Pichia stipitis* NBRC1687 strain as the microorganism, continuous fermentation was carried out with use of a separation membrane. The continuous fermentation was performed for 305 hours under the same conditions as in Example 4 except that the period of preculture was 48 hours and the transmembrane pressure difference was 0.1 to 19.8 kPa, to produce ethanol.

TABLE 23

| | Comparative Example 10 | Comparative Example 11 | Comparative Example 12 | Example 4 |
| --- | --- | --- | --- | --- |
| Fermentation period (hr) | 23 | 40 | 298 | 305 |
| Total glucose fed (g) | 105 | 48 | 596 | 610 |
| Total xylose fed (g) | 0 | 63 | 782 | 801 |
| Total production of ethanol (g) | 50 | 32 | 390 | 548 |
| Unused glucose (g) | 0 | 0 | 0 | 0 |
| Unused xylose (g) | 0 | 0 | 160 | 40 |
| Unused xylose/total amount of filtrate (g/L) | 0 | 0 | 13 | 3 |
| Yield (g/g) | 0.48 | 0.29 | 0.32 | 0.4 |

Comparative Example 13: Production of D-Lactic Acid by Batch Culture of *Candida utilis* Using Hexose as Fermentation Feedstock As the microorganism, the *Candida utilis* CuLpLDH strain, which was prepared by the method disclosed in WO 2010/140602, was used. Batch culture was carried out for 23 hours under the same conditions as in Comparative Example 4 except that the pH was adjusted to 6.0 with 1 N calcium hydroxide and the D-lactic acid fermentation mixed-sugar medium 2 shown in Table 24 was used, to produce D-lactic acid (Table 25).

TABLE 24

| D-Lactic acid fermentation mixed-sugar medium 2 | |
|---|---|
| Glucose | 20 g |
| Xylose | 50 g |
| Yeast extract | 10 g |
| Bactopeptone | 20 g |

Unit (1/Liter)

Comparative Example 14: Production of D-Lactic Acid by Batch Culture of *Candida utilis* Using Mixed Sugar as Fermentation Feedstock Batch culture was carried out for 40 hours under the same conditions as in Comparative Example 5 except that the *Candida utilis* CuLpLDH strain was used as the microorganism; the pH was adjusted to 6.0 with 1 N calcium hydroxide; and the D-lactic acid fermentation mixed-sugar medium 2 shown in Table 24 was used as the culture medium; to produce D-lactic acid (Table 25).

Comparative Example 15: Production of D-Lactic Acid by Continuous Fermentation by *Candida utilis* Using Mixed Sugar as Fermentation Feedstock Continuous fermentation was carried out using the *Candida utilis* CuLpLDH strain as the microorganism, without use of a separation membrane. The continuous fermentation was performed for 290 hours under the same conditions as in Comparative Example 6 except that the period of preculture was 40 hours; the pH was adjusted to 6.0 with 1 N calcium hydroxide; and the D-lactic acid fermentation mixed-sugar medium 2 shown in Table 24 was used as the culture medium; to produce D-lactic acid (Table 25).

Example 7: Production of D-Lactic Acid by Continuous Fermentation by *Candida utilis* Using Mixed Sugar as Fermentation Feedstock, with Use of Separation Membrane 1

Continuous fermentation was carried out using the *Candida utilis* CuLpLDH strain as the microorganism, with use of a separation membrane. The continuous fermentation was performed for 310 hours under the same conditions as in Example 4 except that the period of preculture was 50 hours; the pH was adjusted to 6.0 with 1 N calcium hydroxide; and the D-lactic acid fermentation mixed-sugar medium 2 shown in Table 24 was used as the culture medium, to produce D-lactic acid.

TABLE 25

| | Comparative Example 13 | Comparative Example 14 | Comparative Example 15 | Example 7 |
|---|---|---|---|---|
| Fermentation period (hr) | 23 | 40 | 290 | 310 |
| Total glucose fed (g) | 108 | 49 | 592 | 633 |
| Total xylose fed (g) | 0 | 65 | 785 | 840 |
| Total production of D-lactic acid (g) | 31 | 24 | 295 | 421 |
| Unused glucose (g) | 0 | 0 | 0 | 0 |
| Unused xylose (g) | 0 | 0 | 95 | 20 |
| Unused xylose/total amount of filtrate (g/L) | 0 | 0 | 8 | 2 |
| Yield (g/g) | 0.29 | 0.21 | 0.23 | 0.29 |

Comparative Example 16: Production of Ethanol by Batch Fermentation by *Escherichia coli* Using Hexose as Fermentation Feedstock The *Escherichia coli* KO11 strain was cultured in 2 mL of a preculture medium (20 g/L glucose, 10 g/L yeast extract, 5 g/L tryptone, 5 g/L NaCl) in a test tube at 30° C. overnight (pre-preculture). The obtained culture liquid was inoculated to 50 mL of a preculture medium placed in a 500-mL baffled Erlenmeyer flask, and culture was performed overnight (preculture). The preculture liquid was inoculated to 1 L of the ethanol fermentation medium 2 having the composition shown in Table 26, and batch fermentation was carried out for 16 hours under the following operating conditions while the temperature and the pH were controlled, to produce ethanol (Table 28):
  Culture vessel capacity: 2 (L)
  Temperature adjustment: 30 (° C.)
  Kla: 30 $(h^{-1})$
  pH Adjustment: adjusted to pH 6 with 5 N $Ca(OH)_2$
  Sterilization: the fermentation vessel and media to be used were all subjected to high-pressure steam sterilization by autoclaving at 121° C. for 20 min.

TABLE 26

| Ethanol fermentation medium 2 | |
|---|---|
| Glucose | 40 g |
| Yeast extract | 10 g |
| Tryptone | 5 g |
| NaCl | 5 g |

Unit (1/Liter)

Comparative Example 17: Production of Ethanol by Batch Fermentation by *Escherichia coli* Using Mixed Sugar as Fermentation Feedstock Using the ethanol fermentation mixed-sugar medium 4 having the composition shown in Table 27 as the fermentation medium, batch fermentation was carried out for 24 hours under the same conditions as in Comparative Example 16, to produce ethanol (Table 28).

TABLE 27

| Ethanol fermentation mixed-sugar medium 4 | |
|---|---|
| Glucose | 30 g |
| Xylose | 40 g |
| Yeast extract | 10 g |

TABLE 27-continued

| Ethanol fermentation mixed-sugar medium 4 | |
|---|---|
| Tryptone | 5 g |
| NaCl | 5 g |

Unit (1/Liter)

Comparative Example 18: Production of Ethanol by Continuous Fermentation by *Escherichia coli* Using Mixed Sugar as Fermentation Feedstock Continuous fermentation was carried out using a mixed sugar as the fermentation feedstock, without use of a separation membrane. The *Escherichia coli* KO11 strain was cultured in 2 mL of a preculture medium (20 g/L glucose, 10 g/L yeast extract, 5 g/L tryptone, 5 g/L NaCl) in a test tube at 30° C. overnight (pre-pre-preculture). The obtained culture liquid was inoculated to 50 mL of a preculture medium in a 500-mL baffled Erlenmeyer flask, and culture was performed overnight (pre-preculture). The pre-preculture liquid was inoculated to the ethanol fermentation mixed-sugar medium 4 having the composition shown in Table 27 placed in a continuous culture apparatus (the same apparatus as shown in FIG. 2 of WO 2007/097260 except that the separation membrane element was eliminated), and batch fermentation was carried out for 24 hours under the operating conditions shown below while the temperature and the pH were controlled (preculture). Immediately after completion of the preculture, continuous culture was started to produce ethanol. For supplying the ethanol fermentation mixed-sugar medium 4 having the composition shown in Table 27 and collecting the culture liquid containing the microorganism, a Perista BioMini Pump Type AC-2120 (ATTO) was used to supply the culture medium directly to the culture vessel and to collect the culture liquid containing the microorganism directly from the culture vessel. While the rate of supplying the culture medium was controlled such that the amount of culture liquid in the culture vessel was 1.5 L at a constant rate of collection of the culture liquid containing the microorganism, ethanol production was performed for 290 hours (Table 28).
  Culture vessel capacity: 2 (L)
  Temperature adjustment: 30 (° C.)
  Kla: 30 ($h^{-1}$)
  pH Adjustment: adjusted to pH 6 with 5 N $Ca(OH)_2$
  Rate of collection of the fermentation liquid: 2 L/day
  Sterilization: the fermentation vessel and media to be used were all subjected to high-pressure steam sterilization by autoclaving at 121° C. for 20 min.

Example 8: Production of Ethanol by Continuous Fermentation by *Escherichia coli* Using Mixed Sugar as Fermentation Feedstock, with Use of Separation Membrane Using a mixed sugar as the fermentation feedstock, continuous fermentation was carried out with use of a separation membrane. The *Escherichia coli* KO11 strain was cultured in 2 mL of a preculture medium (20 g/L glucose, 10 g/L yeast extract, 5 g/L tryptone, 5 g/L NaCl) in a test tube at 30° C. overnight (pre-pre-preculture). The obtained culture liquid was inoculated to 50 mL of a preculture medium in a 500-mL baffled Erlenmeyer flask, and culture was performed overnight (pre-preculture). The pre-preculture liquid was inoculated to the ethanol fermentation mixed-sugar medium 4 having the composition shown in Table 27 placed in a continuous fermentation apparatus equipped with an integrated membrane having the properties shown below (the apparatus shown in FIG. 2 of WO 2007/097260), and batch fermentation was carried out for 24 hours under the operating conditions shown below while the temperature and the pH were controlled (preculture). Immediately after completion of the preculture, continuous culture was started to produce ethanol. To supply the ethanol fermentation mixed-sugar medium 4 having the composition shown in Table 27 and filtering the culture liquid, a Perista BioMini Pump Type AC-2120 (ATTO) was used. The culture medium was directly supplied to the culture vessel, and the culture liquid was filtered through an element having an immobilized separation membrane. While the rate of supplying the culture medium was controlled such that the amount of culture liquid in the culture vessel was 1.5 L at a constant rate of filtration of the culture liquid, and the transmembrane pressure difference during filtration was allowed to change within the range of 0.1 to 19.8 kPa, continuous fermentation was performed for 310 hours to produce ethanol (Table 28).
  Fermentation reaction vessel capacity: 2 (L)
  Separation membrane used: polyvinylidene fluoride filtration membrane
  Effective filtration area of the membrane separation element: 473 $cm^2$
  Pure water permeation coefficient of the separation membrane: $50 \times 10^{-9}$ $m^3/m^2/s/Pa$
  Average pore size of the separation membrane: 0.1 μm
  Standard deviation of the average pore size: ±0.035 μm
  Surface roughness of the separation membrane: 0.06 μm
  Temperature adjustment: 30 (° C.)
  pH Adjustment: adjusted to pH 6 with 5 N $Ca(OH)_2$
  Rate of collection of the fermentation liquid: 2 L/day
  Sterilization: the fermentation vessel comprising the separation membrane element, and media to be used were all subjected to high-pressure steam sterilization by autoclaving at 121° C. for 20 min.

TABLE 28

| | Comparative Example 16 | Comparative Example 17 | Comparative Example 18 | Example 8 |
|---|---|---|---|---|
| Fermentation period (hr) | 16 | 24 | 290 | 310 |
| Total glucose fed (g) | 42 | 31 | 749 | 801 |
| Total xylose fed (g) | 0 | 40 | 967 | 1033 |
| Total production of ethanol (g) | 15 | 16 | 246 | 691 |
| Unused glucose (g) | 0 | 0 | 0 | 0 |
| Unused xylose (g) | 0 | 0 | 420 | 15 |
| Unused xylose/total amount of filtrate (g/L) | 0 | 0 | 17 | 1 |
| Yield (g/g) | 0.35 | 0.22 | 0.19 | 0.38 |

Comparative Example 19: Production of L-Lactic Acid by Batch Culture of *Bacillus coagulans* Using Biomass-Derived Sugar Liquid (Glucose, Xylose) as Fermentation Feedstock As the fermentation feedstock, a biomass-derived sugar liquid was used. For preparation of the lactic acid fermentation sugar liquid medium, a cellulose saccharification liquid prepared using a nanofiltration membrane by the preparation method described in Example 2 of WO 2010/067785 was used. The medium was prepared as shown in Table 29 using reagents as appropriate. Batch culture was performed for 70 hours under the same conditions as in Comparative Example 2 except that the different culture medium was used and 4 N KOH was used as the neutralizer, to produce L-lactic acid (Table 30).

TABLE 29

Lactic acid fermentation sugar liquid medium

| | |
|---|---|
| Glucose | 60 g |
| Xylose | 20 g |
| Yeast extract | 5 g |
| Ammonium sulfate | 1 g |
| $K_2HPO_4$ | 0.4 g |

Unit (1/Liter)

Comparative Example 20: Production of L-Lactic Acid by Continuous Culture of *Bacillus coagulans* Using Biomass-Derived Sugar Liquid (Glucose, Xylose) as Fermentation Feedstock As the fermentation feedstock, a biomass-derived sugar liquid was used. As a lactic acid fermentation sugar liquid medium, the culture medium described in Table 29 was used similarly to Comparative Example 19. Continuous culture was performed for 250 hours under the same conditions as in Comparative Example 3 except that the different culture medium was used and 4 N KOH was used as the neutralizer, to produce lactic acid (Table 30).

Example 9: Production of L-Lactic Acid by Continuous Culture of *Bacillus coagulans* Using Biomass-Derived Sugar Liquid (Glucose, Xylose) as Fermentation Feedstock, with Use of Separation Membrane As the fermentation feedstock, a biomass-derived sugar liquid was used. As a lactic acid fermentation sugar liquid medium, the culture medium described in Table 29 was used similarly to Comparative Example 19. Continuous culture was performed using a separation membrane for 260 hours under the same conditions as in Example 1 except that the different culture medium was used and 4 N KOH was used as the neutralizer, to produce L-lactic acid.

TABLE 30

| | Comparative Example 19 | Comparative Example 20 | Example 9 |
|---|---|---|---|
| Fermentation period (hr) | 70 | 250 | 260 |
| Total glucose fed (g) | 60 | 1875 | 1950 |
| Total xylose fed (g) | 20 | 625 | 650 |
| Total production of L-lactic acid (g) | 52 | 1254 | 2176 |
| Unused glucose (g) | 0 | 0 | 0 |
| Unused xylose (g) | 0 | 410 | 40 |
| Unused xylose/total amount of filtrate (g/L) | 0 | 13 | 1 |
| Yield (g/g) | 0.65 | 0.60 | 0.85 |

Comparative Example 21: Production of Ethanol by Batch Culture of *Escherichia coli* Using Biomass-Derived Sugar Liquid (Glucose, Xylose) as Fermentation Feedstock As the fermentation feedstock, a biomass-derived sugar liquid was used. For preparation of the ethanol fermentation sugar liquid medium, a cellulose saccharification liquid prepared using a nanofiltration membrane by the preparation method described in Example 2 of WO 2010/067785 was used. The medium was prepared as shown in Table 31 using reagents as appropriate. Batch culture was performed for 23 hours under the same conditions as in Comparative Example 17 except that the different culture medium was used, to produce ethanol (Table 32).

TABLE 31

Ethanol fermentation sugar liquid medium

| | |
|---|---|
| Glucose | 30 g |
| Xylose | 15 g |
| Yeast extract | 10 g |
| Tryptone | 5 g |
| NaCl | 5 g |

Unit (1/Liter)

Comparative Example 22: Production of Ethanol by Continuous Culture of *Escherichia coli* Using Biomass-Derived Sugar Liquid (Glucose, Xylose) as Fermentation Feedstock Using the culture medium described in Table 31 as an ethanol fermentation sugar liquid medium similarly to Comparative Example 21, continuous culture was performed for 285 hours under the same conditions as in Comparative Example 18, to produce ethanol (Table 32).

Example 10: Production of Ethanol by Continuous Culture of *Escherichia coli* Using Biomass-Derived Sugar Liquid (Glucose, Xylose) as Fermentation Feedstock, with Use of Separation Membrane Using the ethanol fermentation sugar liquid medium shown in Table 27, continuous culture was performed for 295 hours with use of a separation membrane under the same conditions as in Example 8, to produce ethanol.

TABLE 32

| | Comparative Example 21 | Comparative Example 22 | Example 10 |
|---|---|---|---|
| Fermentation period (hr) | 23 | 285 | 295 |
| Total glucose fed (g) | 30 | 713 | 738 |
| Total xylose fed (g) | 15 | 356 | 369 |
| Total production of ethanol (g) | 12 | 193 | 431 |
| Unused glucose (g) | 0 | 0 | 0 |
| Unused xylose (g) | 0 | 230 | 30 |
| Unused xylose/total amount of filtrate (g/L) | 0 | 10 | 1 |
| Yield (g/g) | 0.27 | 0.23 | 0.4 |

Comparative Example 23: Production of Ethanol by Batch Culture of *Candida tropicalis* Using Mixed Sugar (Glucose, Xylose) as Fermentation Feedstock 2

Using the ethanol fermentation mixed-sugar medium 5 shown in Table 33, batch culture was performed for 45 hours under the same conditions as in Comparative Example 4, to produce ethanol (Table 34).

TABLE 33

| Ethanol fermentation mixed-sugar medium 5 | |
|---|---|
| Glucose | 10 g |
| Xylose | 90 g |
| Yeast extract | 10 g |
| Tryptone | 20 g |

Unit (1/Liter)

Comparative Example 24: Production of Ethanol by Continuous Culture of *Candida tropicalis* Using Mixed Sugar as Fermentation Feedstock Using the ethanol fermentation mixed-sugar medium 5 shown in Table 33, continuous culture was performed for 350 hours under the same conditions as in Comparative Example 6, to produce ethanol (Table 34).

Example 11: Production of Ethanol by Continuous Culture of *Candida tropicalis* Using Mixed Sugar (Glucose, Xylose) as Fermentation Feedstock, with Use of Separation Membrane 2

Using the ethanol fermentation mixed-sugar medium 5 shown in Table 33, continuous culture was carried out for 360 hours under the same conditions as in Example 4, to produce ethanol (Table 34).

Comparative Example 24: Production of Ethanol by Continuous Culture of *Candida tropicalis* Using Mixed Sugar as Fermentation Feedstock Using the *Candida tropicalis* NBRC0199 strain, continuous fermentation was performed with use of a ceramic separation membrane. The culture medium shown in Table 33 was used as the fermentation medium. The *Candida tropicalis* NBRC0199 strain was cultured in 2 mL of YPD medium in a test tube at 30° C. overnight with shaking (pre-pre-preculture). The obtained culture liquid was inoculated to 50 mL of YPD medium in a 500-mL baffled Erlenmeyer flask, and culture was performed overnight with shaking (pre-preculture). The pre-preculture liquid was inoculated to 1.5 L of YPDX medium placed in a membrane-separation-type continuous fermentation apparatus (the apparatus shown in FIG. 12 of WO 2012/086763), and culture was performed for 36 hours with stirring at 800 rpm by the stirrer attached to the culture vessel while the aeration rate and the temperature in the culture vessel were controlled (preculture). Immediately after completion of the preculture, continuous culture was started. While the transmembrane pressure difference during filtration was controlled at not more than 500 kPa, continuous culture was carried out for 400 hours to produce ethanol (Table 34).

Culture vessel capacity: 2 L
Separation membrane used: Celfit microfiltration membrane Monolith φ4-19 (NGK Insulators, Ltd.)
Length of the membrane separation element: 500 mm
Average pore size of the separation membrane: 0.1 μm
Temperature adjustment: 30° C.
Aeration in the fermentation reaction vessel: 100 (mL/min)
Stirring rate in the fermentation reaction vessel: 800 (rpm)
pH Adjustment: none

TABLE 34

| | Comparative Example 23 | Comparative Example 24 | Example 11 | Example 12 |
|---|---|---|---|---|
| Fermentation period (hr) | 45 | 350 | 360 | 400 |
| Total glucose fed (g) | 16 | 146 | 150 | 100 |
| Total xylose fed (g) | 136 | 1313 | 1350 | 900 |
| Total production of ethanol (g) | 8 | 67 | 175 | 125 |
| Unused glucose (g) | 0 | 0 | 0 | 0 |
| Unused xylose (g) | 0 | 125 | 45 | 40 |
| Unused xylose/total amount of filtrate (g/L) | 0 | 8.57 | 3 | 4.0 |
| Yield (g/g) | 0.05 | 0.05 | 0.12 | 0.13 |

Example 13: Production of 2,3-Butanediol by Continuous Culture of *Paenibacillus polymyxa* Using Mixed Sugar (Glucose, Xylose) as Fermentation Feedstock, with Use of Ceramic Separation Membrane 2

Using the *Paenibacillus polymyxa* ATCC12321 strain, continuous fermentation was carried out with use of a ceramic separation membrane. The *Paenibacillus polymyxa* ATCC12321 strain was cultured in 2 mL of a preculture medium (5 g/L glucose, 5 g/L peptone, 3 g/L yeast extract, 3 g/L malt extract) in a test tube at 30° C. overnight (pre-pre-preculture). The obtained culture liquid was inoculated to 50 mL of a preculture medium in a 500-mL baffled Erlenmeyer flask, and culture was performed overnight (pre-preculture). The pre-preculture liquid was inoculated to the 2,3-butanediol fermentation mixed-sugar medium having the composition shown in Table 16 placed in a continuous culture apparatus (the apparatus shown in FIG. 2 of WO 2007/097260), and batch fermentation was carried out for 30 hours under the operating conditions shown below while the temperature and the pH were controlled (preculture). Immediately after completion of the preculture, continuous culture was started using the 2,3-butanediol fermentation mixed-sugar medium having the composition shown in Table 16 to produce 2,3-butanediol. While the transmembrane pressure difference during filtration was controlled at not more than 500 kPa, continuous culture was carried out for 300 hours to produce 2,3-butanediol (Table 35).

Fermenter capacity: 2 (L)
Separation membrane used: Celfit microfiltration membrane Monolith φ4-19 (NGK Insulators, Ltd.)
Length of the membrane separation element: 500 mm
Average pore size of the separation membrane: 0.1 μm
Temperature adjustment: 30 (° C.)
Aeration in the fermentation reaction vessel: 100 (mL/min)
Stirring rate in the fermentation reaction vessel: 800 (rpm)
pH Adjustment: adjusted to pH 6.5 with 5 N Ca(OH)$_2$

TABLE 35

| | Example 13 |
|---|---|
| Fermentation period (hr) | 310 |
| Total glucose fed (g) | 129 |
| Total xylose fed (g) | 258 |
| Total production of 2,3-butanediol (g) | 111 |
| Unused glucose (g) | 0 |
| Unused xylose (g) | 5 |
| Unused xylose/total amount of filtrate (g/L) | 0.8 |
| Yield (g/g) | 0.29 |

INDUSTRIAL APPLICABILITY

The efficiencies of fermentation production of various chemical products using a fermentation feedstock containing pentose and hexose can be largely increased with our methods.

The invention claimed is:

1. A method of producing a chemical product by continuous fermentation comprising:
    filtering a culture liquid of a microorganism(s) comprising yeast or bacteria through a separation membrane;
    retaining unfiltered liquid in, or refluxing unfiltered liquid to, the culture liquid;
continuously adding a fermentation feedstock comprising a mixed sugar of hexose and pentose to the culture liquid; and
    recovering a product in the filtrate;
    wherein
        said microorganism(s) is/are a microorganism(s) that metabolizes(s) hexose and pentose and undergo(es) catabolite repression, whose consumption of pentose is suppressed when a fermentation feedstock comprising a mixed sugar containing hexose and pentose is used,
    the total sugar concentration in the fermentation feedstock is 60 g/L to 500 g/L,
    a weight ratio between the hexose and the pentose contained in said fermentation feedstock is 1:9 to 9:1, and
    a concentration of said pentose in a total amount of said filtrate is not more than 5 g/L, and
    the product is (i) an alcohol selected from the group consisting of ethanol, 1,3-propanediol 1,3-butanediol, 2,3-butanediol, 1,4-butanediol, glycerol, butanol, isobutanol, 2-butanol, and isopropanol, (ii) an organic acid selected from the group consisting of acetic acid, lactic acid, adipic acid, pyruvic acid, succinic acid, malic acid, itaconic acid, and citric acid, or (iii) a free amino acid.

2. The method according to claim 1, wherein the pentose is xylose and the hexose is glucose.

3. The method according to claim 1, wherein the total sugar concentration in the fermentation feedstock is 60 g/L to 300 g/L.

* * * * *